(12) United States Patent
Levy et al.

(10) Patent No.: US 10,004,761 B2
(45) Date of Patent: Jun. 26, 2018

(54) MALODOR NEUTRALIZING COMPOSITION

(71) Applicants: Mark M. Levy, RaAnana (IL); Zvi Nevo, Herzlia (IL); Samuel Levin, Tel-Aviv (IL)

(72) Inventors: Mark M. Levy, RaAnana (IL); Zvi Nevo, Herzlia (IL); Samuel Levin, Tel-Aviv (IL)

(*) Notice: Subject to any disclaimer, the term of this patent is extended or adjusted under 35 U.S.C. 154(b) by 0 days. days.

(21) Appl. No.: 15/628,796

(22) Filed: Jun. 21, 2017

(65) Prior Publication Data
US 2017/0360822 A1 Dec. 21, 2017

Related U.S. Application Data

(60) Provisional application No. 62/352,610, filed on Jun. 21, 2016.

(51) Int. Cl.
| | |
|---|---|
| *A61K 31/728* | (2006.01) |
| *A61K 31/11* | (2006.01) |
| *A61K 31/198* | (2006.01) |
| *A61Q 19/00* | (2006.01) |
| *A61K 8/33* | (2006.01) |
| *A61K 8/44* | (2006.01) |
| *A61Q 15/00* | (2006.01) |
| *A61K 8/73* | (2006.01) |
| *A61K 45/06* | (2006.01) |
| *A61K 9/00* | (2006.01) |
| *A61K 47/20* | (2006.01) |
| *A61K 47/36* | (2006.01) |

(52) U.S. Cl.
CPC ............ *A61K 31/728* (2013.01); *A61K 8/33* (2013.01); *A61K 8/447* (2013.01); *A61K 8/735* (2013.01); *A61K 31/198* (2013.01); *A61K 45/06* (2013.01); *A61Q 15/00* (2013.01); *A61K 9/0034* (2013.01); *A61K 47/20* (2013.01); *A61K 47/36* (2013.01)

(58) Field of Classification Search
CPC .... A61K 31/728; A61K 31/11; A61K 31/198; A61Q 19/00
USPC ........................................................ 514/562
See application file for complete search history.

(56) References Cited

U.S. PATENT DOCUMENTS

| | | | |
|---|---|---|---|
| 4,840,792 A * | 6/1989 | Joulain ................ | A01K 1/0152 424/405 |
| 5,733,535 A * | 3/1998 | Hollingshead ........ | A61K 8/447 424/400 |
| 5,861,146 A | 1/1999 | Peterson et al. | |
| 7,321,000 B2 | 1/2008 | Boldrini et al. | |
| 7,727,537 B2 | 6/2010 | Modi | |
| 8,784,893 B2 | 1/2014 | Daniloff et al. | |
| 8,835,511 B2 | 9/2014 | Carlucci et al. | |
| 8,992,889 B2 | 3/2015 | Woo et al. | |
| 2002/0001602 A1 * | 1/2002 | Afriat ................... | A61K 8/064 424/401 |
| 2012/0226248 A1 | 9/2012 | Caputi et al. | |
| 2013/0136712 A1 | 5/2013 | Woo et al. | |
| 2013/0158491 A1 | 6/2013 | Caputi et al. | |
| 2013/0266642 A1 | 10/2013 | Hollingshead et al. | |
| 2014/0186285 A1 | 7/2014 | Woo et al. | |
| 2014/0377207 A1 | 12/2014 | Scavone et al. | |
| 2014/0378920 A1 | 12/2014 | Scavone et al. | |
| 2015/0093351 A1 | 4/2015 | Horenziak et al. | |
| 2015/0297482 A1 | 10/2015 | Troccaz et al. | |

FOREIGN PATENT DOCUMENTS

| | | |
|---|---|---|
| EP | 1886698 | 2/2008 |
| EP | 2263703 | 12/2010 |
| WO | WO 2007/113778 | 10/2007 |

OTHER PUBLICATIONS

Stenzaly-Achtert et al. Skin Research and Technology, (2000), 6(2), p. 87-91.*
Castro et al. "Categorical Dimensions of Human Odor Descriptor Space Revealed by Non-Negative Matrix Factorization", PLOS ONE, 8(9): e73289-1-e73289-16, Sep. 18, 2003.
Shimizu et al. "Bonitos With Low Content of Malodorous Trimethylamine as Palliative Care for Self-Reported Japanese Trimethylaminuria Subjects", Drug Metabolism and Pharmacokinetics, 24(6): 549-552, Dec. 31, 2009.
Sunitha et al. "Inhibition of Hyaluronidase by N-Acetyl Cysteine and Glutathione: Role of Thiol Group in Hyaluronan Protection", International Journal of Biological Macromolecules, 55: 39-48, Published Online Jan. 8, 2013.
Yamazaki et al. "Effects of the Dietary Supplements, Activated Charcoal and Copper Chlorophyllin, on Urinary Excretion of Trimethylamine in Japanese Trimethylaminuria Patients", Life Sciences, 74(22): 2739-2747, Apr. 16, 2004.

* cited by examiner

*Primary Examiner* — Yong Chu

(57) ABSTRACT

A composition suitable for treating a variety of medical, aesthetic and cosmetic conditions in mucous membranes and occluded skin areas, comprising hyaluronic acid, N-acetyl-cysteine, an active agent and set to pH of less than 6, which is characterized by high in vivo stability, is disclosed, as well as uses thereof in temporally extended delivery of active agent to mucous membrane in bodily sites.

9 Claims, No Drawings

MALODOR NEUTRALIZING COMPOSITION

RELATED APPLICATION

This application claims the benefit of priority under 35 USC 119(e) of U.S. Provisional Patent Application No. 62/352,610 filed on Jun. 21, 2016, the contents of which are incorporated herein by reference in their entirety.

FIELD AND BACKGROUND OF THE INVENTION

The present invention, in some embodiments thereof, relates to pharmaceutical and/or cosmetic compositions, and more particularly, but not exclusively, to stabilize compositions for neutralizing malodor in mucous membranes and occluded skin areas.

Mucous membranes secrete an aqueous fluid rich in glycoproteins that normally has no offensive odor. For example, normal vaginal discharge may change consistency and color during the menstrual cycle but typically is it is not characterized by malodor. Nonetheless, unpleasant malodor in the genital area and around it is quite common in women, and other than being a source of embarrassment. It is oftentimes a symptom of one or more medical conditions, including bacterial vaginosis, trichomoniasis, yeast infection, gonorrhea and chlamydia, pelvic inflammatory disease, and human papillomavirus (HPV) or cervical cancer. In certain cases it is difficult to diagnose and to treat abnormal malodorous vaginal discharge having an atypical high pH. In general, vaginal pathology is curable by several cycles of anti-bacterial and anti-fungal medications. An additional approach consists on introducing an acidic flora to lower the local pH.

Severe mucous membrane malodor may occur even without a microorganism infection, and some are related to metabolic deficiencies and genetic disposition, such as in the case of trimethylaminuria. Currently there is no cure or approved drug to treat trimethylaminuria, but symptoms can be improved by making certain lifestyle changes, refreshing agents, common vitamins, watery douches, dietary restrictions, antibiotics, laxatives, activated charcoal, copper chlorophyllin, Apple cider vinegar, soaked tampons, probiotic pills, alum stick, cranberries, femunol preparation, enzara preparation, and the likes. The refreshing procedures were followed by powdered-perfuming techniques with balsamic fragrances, believing to mask or camouflage the bad vaginal smells.

Nonetheless, most mucous membrane malodor arise from one form or another of chemical degradation of amino acids, proteins and other nitrogen-rich and sulfur-rich naturally occurring substances. The main family of these compounds is the primary amines and the polyamines family, and the second major family is that of the sulfides. The malodor generated by both these families can potentially be neutralized by chemical agents. One exemplary source of the offensive smells of the vaginal-genital regions, resulting from proteins breakdown, is trimethylamine (TMA), which is the cause of the so-called fishy smell syndrome. TMA may accumulate in individuals that have a metabolic deficiency of an enzyme that oxidizes TMA to an odorless molecule easily soluble and drained out through the kidney.

Formulations for treating malodors associated with amine compounds have been suggested in the literature, and include harnessing the tendency of aldehydes to react with amines in what is known as Schiff base forming reaction, wherein an amine and an aldehyde interact to form an imine, to neutralize the amines, thereby mitigating the malodor problem. Exemplary background art for such approach include U.S. Pat. Nos. 9,055,849, 8,992,889, 8,674,167, 8,461,089 and 8,357,359, and U.S. Patent Application Publication Nos. 2014/0186285, 2013/0247941, 2013/0136712, 2013/0121950, 2011/0305659, 2011/0268667, 2011/0152804, 2011/0152157, 2011/0150817, 2011/0150816, 2011/0150815 and 2011/0150814. Additional background art include U.S. Pat. Nos. 5,733,535, 5,861,146, 5,939,060 and 8,835,511, U.S. Patent Application Publication Nos. 2012/0226248, 2013/0158491, 2013/0266642, 2014/0377207, 2014/0378920 and 2015/0093351, WO 2007113778, and EP1886698, EP2251016 and EP2263703.

Hyaluronic acid or its salt (HA) is an anionic, non-sulfated glycosaminoglycan that is naturally occurring in the body. It has been used extensively in many cosmetic and therapeutic applications as a filler and lubricant. Hyaluronic acid would be considered ideal as a carrier for compositions aimed for use in bodily sites that are prone to malodor, particularly vaginal mucus membranes that would benefit from its low pH. However, its use on mucus membrane is rather limited due to its low stability under physiological conditions caused mainly by enzymatic degradation, e.g., by hyaluronidase.

Attempts of overcoming the limitations associated with HA application, due to its rapid enzymatic degradation, typically involve introducing synthetic cross-linkers, for providing HA composite with reduced biodegradation rate, using high MW HA preparations, and employing specific or non-specific inhibitors of hyaluronidase. Hyaluronic acid degrading enzymes and inhibitors of the same have been described in the literature [see, for example, Sunitha, K. et al., *Int J Biol Macromol.*, 2013, 55, pp. 39-46].

One of the inhibitors of hyaluronidase is N-acetylcysteine (NAC). NAC is a long-time used mucolytic medication, and is also known as exhibiting an anti-oxidative activity, as an antidote for acetaminophen overdose and as a chelating agent in systemic use. The use of systemic NAC, or NAC derivatives, alone or in combination with other antioxidants has been disclosed, for example, in WO 2010/086736, WO 2001/056572A1, WO 2006/116353A2, WO 2006/116353A3, WO 2011/044230A2, U.S. Pat. Nos. 6,420,429, 6,369,106 and 5,962,421, and U.S. Patent Applications having Publications Nos. 2011/0288134 and 2011/0244045. Topical application of NAC has been proposed as a method for prevention of sunburn in EP219455, for regulation of existing skin wrinkles and atrophy in U.S. Pat. No. 5,296,500, and for inhibition/prevention of photoaging-stain spots, when combined with a sun-blocking agent, to undamaged skin.

U.S. Patent Application Publication No. 2010/0004198 teaches polysaccharide (e.g., HA) formulations having increased longevity, which comprise the polysaccharide and an inhibitor of its degradation. The inhibitor can be a GAG, an antioxidant, a flavonoid, and the like.

U.S. Patent Application Publication No. 2003/0162732 teaches chemical complexes of cysteine or derivatives of cysteine and an amino sugar, as well as pharmaceutical compositions and dietary supplements comprising such complexes.

U.S. Pat. No. 5,804,594 teaches orally administered compositions comprising a sugar compound that is converted to a glycosaminoglycan in vivo, such as HA, an antioxidant, at least one amino acid and a transition metal, and their use in treating skin conditions.

Cosmetic and/or filler compositions comprising HA and optionally NAC, typically as an anti-oxidant, are also disclosed in U.S. Patent Application Publication Nos. 2009/0017091, 2005/0266064 and 2009/0143348, WO 2009/005790 and WO 2008/070893.

Additional background art includes WO 2006/135479, WO 2009/011849, WO 2006/121521, and WO 2006/121518, U.S. Pat. Nos. 5,707,635, 6,497,887, 7,321,000 and 8,784,893, U.S. Patent Application Publication Nos. 2004/0248847, 2005/0266064, 2011/0033540, 2013/0309217, 2014/0212388 and 2015/0190412 and WO 2003/011249.

SUMMARY OF THE INVENTION

The present invention is drawn to a composition suitable for treating a variety of medical, aesthetic and cosmetic conditions in mucous membranes and occluded skin areas, comprising hyaluronic acid or salts thereof, N-acetylcysteine or derivative and analog thereof and a malodor neutralizing agent, and set to pH of less than 6, which is characterized by high in vivo stability. In some embodiments, the malodor neutralizing agent is selected to chemically react with malodorous substances, thereby neutralizing the source of malodor. The present invention is also directed at various uses of the composition for treating malodor and bacterial and fungal infections in mucous membranes and occluded skin areas of various bodily sites, effected by applying the composition provided herein, which acts as temporally extended delivery system of therapeutically and/or cosmetically active agents.

In contrast to the currently available solutions where the absorbent substances for controlling and reducing malodors are embedded within matrices of personal hygiene articles, the composition provided herein is formulated for reducing malodors in vaginal and genital regions, and further formulated for direct application thereof on the mucus membranes of the vulva, labia and vaginal walls. The composition contains volatile and non-volatile malodor neutralizing agents that chemically react with malodorous chemicals that are typically amine-containing compounds derived from proteins and amino acid breakdown in/on the mucus membrane, and thereby form a non-odorous substance. A chemically stable, pharmaceutically and cosmetically acceptable hydrogel-forming substance, which is also suitably viscous and acidic, comprising a combination of aqueous hyaluronic acid gel and N-acetylcysteine, serves as a long lasting carrier for the neutralizing agents. The combination of hyaluronic acid gel and N-acetylcysteine is selected such that N-acetylcysteine acts as an inhibitor against hyaluronic acid enzymatic degradation. The neutralizing agents are selected from a family of suitable aldehydes, such as the exemplary myrac aldehyde, which are gradually released and interacts with the malodorous substances, thereby neutralizing the malodors. The herein-provided composition is characterized by a sticky and long standing topical presence after application. The composition can be supplemented with other substances such as perfumes, essences, dyes, colorants, preservatives, thickening agents, oils, and other natural or artificial materials for further characterization. In some embodiments, the composition can be formulated for higher viscosity (less fluidic state) or encapsulated to allow placement of the composition inside bodily cavities.

According to an aspect of some embodiments of the present invention, there is provided a malodor neutralizing composition that includes hyaluronic acid or a salt thereof (HA), N-acetyl cysteine or a pharmaceutically or cosmetically acceptable derivative thereof (NAC), and a pharmaceutically or cosmetically acceptable malodor neutralizing agent.

In some embodiments, the concentration of the HA ranges from 0.1% to 5% by weight of the total weight of the composition.

In some embodiments, the concentration of the NAC is an inhibitory effective amount with respect to enzymatic degradation of the HA.

In some embodiments, the inhibitory effective amount ranges from 0.1% to 10% by weight of the total weight of the composition.

In some embodiments, the concentration of the malodor neutralizing agent ranges from 0.1% to 10% by weight of the total weight of the composition.

In some embodiments, the aldehyde is selected from the group consisting of Myrac aldehyde (4-(4-methylpent-3-enyl)cyclohex-3-ene-1-carbaldehyde), Lauric Aldehyde, Jasmal Aldehyde, Melonal Aldehyde, 2,4-Decadienal, 2,4-Dimethyl-3-cyclohexene carboxaldehyde, 2,4-dimethylbenzaldehyde, 2,4-hexadienal, 2,4-octadienal, 2,6,6-trimethyl-1-cyclohexene-1-acetaldehyde, 2,6-dimethyl 5-heptenal, 2,6-Nonadienal, 2-Dodecanal, 2-Ethylbutyraldehyde, 2-isopropyl-5-methyl-2-hexenal, 2-methyl butanal, 2-methyl butyraldehyde, 2-Methyl Valeraldehyde, 2-Methyl-2-pentenal, 2-methyl-3-(p-isopropylphenyl)-propionaldehyde, 2-methyl-3-tolylproionaldehyde, 2-methylpentenal, 2-pentyl-3-phenylpropenoic aldehyde, 2-phenylproprionaldehyde, 3-(p-isopropylphenyl)-propionaldehyde, 3,7-dimethyl-2,6-octadien-1-al), 3-Methyl-2-butenal, 3-methyl-4-phenyl propanal, 3-phenyl butanal, 3-phenyl-2-propenal, 3-phenylpropanal, 3-phenylpropionaldehyde, 4-dimethylbenzenepropanal, 4-ethyl benzaldehyde, Acalea (p-methyl-alpha-pentylcinnamaldehyde), acetaldehyde (ethanal), Adoxal (2,6,10-Trimethyl-9-undecenal), aldehyde C-11 MOA (2-methyl deca-1-al), aldehyde C12 MNA (2-methyl-1-undecanal), alpha-Amylcinnamic aldehyde, alpha-hexyl-cinnamaldehyde (2-hexyl 3-phenyl propenal), alpha-Methylcinnamaldehyde (2-methyl 3-pheny propenal), amylaldehyde, Anisaldehyde (p-methoxybenzene aldehyde), anisylpropanal 4-methoxy-alpha-methyl benzenepropanal (2-anisylidene propanal), Benzaldehyde, benzenepropanal (4-tert-butyl-alpha-methyl-hydrocinnamaldehyde), beta methyl Benzenepropanal, beta-cyclocitral, Bourgeonal (4-t-butylbenzenepropionaldehyde), butyraldehyde, Canthoxal, Catechaldehyde (3,4-dihydroxybenzaldehyde), Cinnamaldehyde (Cinnamic aldehyde), cis or trans-Heptenal, Citral, Citronellal (3,7-dimethyl 6-octenal), citronellal hydrate (7-hydroxy-3,7-dimethyl octan-1-al), Citronellyl oxyacetaldehyde, Corps 4322, Corps Iris, Cuminaldehyde (4-isopropyl benzaldehyde), Cyclal C (2,4-dimethyl-3-cyclohexen-1-carbaldehyde), cyclamen aldehyde, Cyclemax, Cyclocitral, Cyclosal, Cylcemone A (1,2,3,4,5,6,7,8-octahydro-8,8-dimethyl-2-naphthaldehyde), Cymal, Decanal, Decenal (2-,4-), Dihydrocitronellal (3,7-dimethyl octan-1-al), dimethyloctadienal, Dupical, Ethoxybenzaldehyde, Ethyl vanillin (3-ethoxy 4-hydroxybenzaldehyde), Floralozone, Florhydral (3-(3-Isopropyl-phenyl)-butyraldehyde), formyl Tricyclodecan, Geranial, Glutaraldehyde (Glutaric aldehyde), Helional (alpha-methyl-3,4-(methylenedioxy)-hydrocinnamaldehyde, Heliotropin (piperonal) 3,4-Methylene dioxy benzaldehyde, Heptenal, Hexenal (cis, trans, 2-, 3-), Hexyl Cinnamic aldehyde, hydrocinnamaldehyde, Hydrotropaldehyde, Hydroxycitronellal, Intreleven aldehyde (undec-10-en-1-al), Iso Cyclocitral (2,4,6-trimethyl-3-cyclohexene-1-carboxaldehyde), isobutyraldehyde, isovaleraldehyde (3-methyl butyraldehyde), Jasmonal H (alpha-n-hexyl-cinnamaldehyde), Jasmorange, Lauric aldehyde, Ligustral, Lilestralis 33 (2-methyl-4-t-butylphenyl)propanal), lilial, Lime aldehyde (Alpha-methyl-p-isopropyl phenyl propyl aldehyde), Lyral (4-(4-hydroxy-4-methyl pentyl)-3-cyclohexene-1-carboxaldehyde), lysmeral, Maceal, Mandarin aldehyde, Mefranal (3-methyl-5-phenyl pentanal), Melafleur (1,2,3,4,5,6,7,8-octahydro-8,8-dimethyl-2-naphthaldehyde), Melonal (2,6-Dimethyl-5-Heptenal), Methoxy Melonal (6-methoxy-2,6-dimethylheptanal), methoxycinnamaldehyde (trans-4-methoxycinnamaldehyde), Methyl Nonyl Acetaldehyde, Methyl Octyl Acetaldehyde, methylbutyraldehyde, methylcinnamaldehyde, Methylthiobutanal, Muguet aldehyde 50 (3,7-dimethyl-6-octenyl)oxyacetaldehyde), Myrac aldehyde isohexenyl cyclohexenyl-carboxaldehyde, Myrtenal (pin-2-ene-1-carbaldehyde), Neral, Nonanal, Nonenal (2-, 6-), Octanal, Octenal, Onicidal (2,6,10-trimethyl-5,9-undecadien-1-al), P.T. Bucinal, para-ethyl-alpha,alpha-dimethyl hydrocinnamaldehyde, pentanal, Pentanedial, Perillaldehyde L-4 (1-methylethenyl)-1-cyclohexene-1-carboxaldehyde), phenyl Butenal (2-phenyl 2-butenal), phenyl propenal, phenylacetaldehyde, Pino acetaldehyde, Precylcemone B (1-cyclohexene-1-carboxaldehyde), propionaldehyde (propanal), p-Tolylacetaldehyde (4-methylphenylacetaldehyde), pyruvaldehyde, Safranal (2,6,6-trimethyl-1,3-diene methanal), Salicylaldehyde (2-hydroxy benzaldehyde), satinaldehyde, Scentenal (octahydro-5-methoxy-4,7-Methano-1H-indene-2-carboxaldehyde), Syringaldehyde (3,5-dimethoxy 4-hydroxybenzaldehyde), tricyclodecylidenebutanal (4-Tricyclo5210-2,6decylidene-8butanal), Tridecanal, Trifernal, Triplal, Trivertal (2,4-dimethyl-3-cyclohexene-1-carboxaldehyde), Undecenal (2-, 10-), valeraldehyde, Vanillin (4-methoxy 3-hydroxy benzaldehyde), Veratraldehyde (3,4-dimethoxybenzaldehyde), Vernaldehyde (1-Methyl-4-(4-methylpentyl)-3-cyclohexenecarbaldehyde), Vertocitral dimethyl tetrahydrobenzene aldehyde (2,4-dimethyl-3-cyclohexene-1-carboxaldehyde), and any combination or mixture thereof.

In some embodiments, the malodor neutralizing agent is a non-fragrant aldehyde.

In some embodiments, the malodor neutralizing agent is a fragrant aldehyde.

In some embodiments, the fragrant aldehyde is selected from the group consisting of Myrac aldehyde, floral super, 2-ethoxy Benzylaldehyde, 2-isopropyl-5-methyl-2-hexenal, 5-methyl Furfural, 5-methyl-thiophene-carboxaldehyde, p-anisaldehyde, benzylaldehyde, cinnamic aldehyde, decyl aldehyde, Ligustral, Lyral, Melonal, o-anisaldehyde, P.T. Bucinal, thiophene carboxaldehyde, trans-4-decenal, trans 2,4-nonadienal, undecyl aldehyde, Helional (alpha-methyl-3,4-(methylenedioxy)-hydrocinnamaldehyde), Florhydral, Undecylenic Aldehyde, Adoxal (2,6,10-Trimethyl-9-undecenal), Bourgeonal (4-t-butylbenzenepropionaldehyde), Cymal, Florhydral (3-(3-isopropyl-phenyl)-butyraldehyde), Citronellal (3,7-dimethyl 6-octenal), Floralozone (para-ethyl-alpha,alpha-dimethyl hydrocinnamaldehyde), Floral Super, Pino Acetaldehyde, Styrax Coeur, Lauric Aldehyde, Jasmal Aldehyde, Melonal Aldehyde, lily aldehyde, trifernal, and any mixtures thereof.

In some embodiments, the composition presented herein is having a pH lower than 6.

According to another aspect of some embodiments of the present invention, there is provided a composition that includes hyaluronic acid sodium salt, N-acetylcysteine, myrac aldehyde and water, and having a pH equal or lower than 6.

In some embodiments, the concentration of the hyaluronic acid sodium salt ranges from 0.1% to 5% by weight of the total weight of the composition.

In some embodiments, the concentration of the N-acetylcysteine ranges from 0.1% to 10% by weight of the total weight of the composition.

In some embodiments, the concentration of the myrac aldehyde ranges from 0.1% to 10% by weight of the total weight of the composition.

In some embodiments, the composition further includes an additional agent selected from the group consisting of a fragrance, an antimicrobial agent, a bioactive agent, a spermicide, a preservative, a pH adjusting agent, a lubricant, a skin aid, an anti-pruritic agent, a colorant, a diluent, a surfactant and a wetting agent.

In some embodiments, the composition is formulated for topical application on mucous membranes and occluded skin areas.

According to another aspect of some embodiments of the present invention, there is provided a use of the composition presented herein for neutralizing malodor in mucous membranes and occluded skin areas.

According to another aspect of some embodiments of the present invention, there is provided a method of neutralizing malodor in a subject in need thereof, that includes contacting mucous membranes and occluded skin areas with the composition presented herein.

According to another aspect of some embodiments of the present invention, there is provided a carrier composition that includes hyaluronic acid or a salt thereof (HA), N-acetyl cysteine or a pharmaceutically or cosmetically acceptable derivative thereof (NAC), the composition is characterized by a pH lower than 6 and a viscosity that ranges from 5 to 30 Pa·s.

In some embodiments, the carrier composition further includes an additional agent selected from the group consisting of an aldehyde, a bioactive agent, a spermicide, a fragrance, an antimicrobial agent, a preservative, a pH adjusting agent, a lubricant, a skin aid, an anti-pruritic agent, a colorant, a diluent, a surfactant and a wetting agent.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

As used herein the term "about" refers to ±10%.

The terms "comprises", "comprising", "includes", "including", "having" and their conjugates mean "including but not limited to".

The term "consisting of" means "including and limited to."

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the phrases "substantially devoid of" and/or "essentially devoid of" in the context of a certain substance, refer to a composition that is totally devoid of this substance or includes less than about 5, 1, 0.5 or 0.1 percent of the substance by total weight or volume of the composition. Alternatively, the phrases "substantially devoid of" and/or "essentially devoid of" in the context of a certain property or characteristic, refer to a process, a composition, a structure or an article that is totally devoid of the property or characteristic or characterized by less than about 5, 1, 0.5 or 0.1 percent of the property or characteristic, compared to a given standard.

The term "exemplary" is used herein to mean "serving as an example, instance or illustration". Any embodiment described as "exemplary" is not necessarily to be construed as preferred or advantageous over other embodiments and/or to exclude the incorporation of features from other embodiments.

The words "optionally" or "alternatively" are used herein to mean "is provided in some embodiments and not provided in other embodiments". Any particular embodiment of the invention may include a plurality of "optional" features unless such features conflict.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination or as suitable in any other described embodiment of the invention. Certain features described in the context of various embodiments are not to be considered essential features of those embodiments, unless the embodiment is inoperative without those elements.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination or as suitable in any other described embodiment of the invention. Certain features described in the context of various embodiments are not to be considered essential features of those embodiments, unless the embodiment is inoperative without those elements.

It is expected that during the life of a patent maturing from this application many relevant malodor neutralizing compositions will be developed and the scope of the phrase "malodor neutralizing composition" is intended to include all such new technologies a priori.

DESCRIPTION OF SPECIFIC EMBODIMENTS
OF THE INVENTION

The present invention, in some embodiments thereof, relates to pharmaceutical and/or cosmetic compositions, and more particularly, but not exclusively, to stabilize compositions for neutralizing malodor in mucous membranes and occluded skin areas.

The principles and operation of the present invention may be better understood with reference to the accompanying descriptions.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

As presented hereinabove, attempts to deal with bodily malodor, and particularly malodor originating from the degradation of amine compounds, has been tried by contacting the source of the odor with aldehydes in an attempt to form an odorless and otherwise benign imine (Schiff base). These attempts have been partially successful in certain conditions, but when the treated site is a mucus membrane, known compositions failed to deliver the remedy sustainably for a number of reasons, including lack of stability of the carrier, irritation and general lack of efficacy due to the prevailing conditions. Hence, the problem of providing a sustained/prolonged solution to the problem of malodorous genitalia regions has not been solved.

While searching for a comprehensive solution to the problem of malodor of mucus membranes and occluded skin areas in the body, the present inventors have contemplated the use of hyaluronic acid or salts thereof, jointly referred to herein as HA, as a suitable carrier of a malodor source neutralizer. The fact that HA is naturally acidic has been seen as positive for both the mucus membrane ability to fight-off bacteria, the presence of which is oftentimes the source of the malodor. However, HA has a rather limited effective period of time in vivo primarily due to enzymatic degradation.

While considering the problems of biodegradation of HA, the present inventors have found that N-acetylcysteine (NAC) is an effective inhibitor of HA-degrading enzymes. It was found that inhibitory concentrations of NAC in aqueous HA gels can be reached well below pharmaceutically accepted NAC concentrations. It was further found that NAC is effective in lowering the pH of the HA carrier to optimal odor-neutralizing levels. Low (acidic) pH levels are knows to diminish bacterial development in mucus membranes and occluded skin areas and promote Schiff base formation reaction, which is a reaction by which aldehydes react with amines to form imines. As known in the art, pH of about 5 is optimal for imine formation; at higher pH there is insufficient acid present for imine formation, and at much lower pH the amine will be protonated, rendering it unable to undertake a nucleophilic attack on the aldehyde's carbonyl carbon.

Thus, the present invention relates to compositions and methods of reducing body and/or vaginal malodor comprising application of a malodor neutralizing composition based on HA, NAC and a malodor neutralizing agent. The present invention also relates to methods of use of an article of manufacture comprising the compositions presented herein.

The term "occluded skin", as used herein, refers to regions of a human or mammalian body covered by undergarments, such as the pelvic area, panty-area, and bra-line; and skin-folds or intertriginous regions, where there is continuing skin to skin contact. The term "excess moisture", as used herein, means an undesirable and/or unhealthy level of body fluids deposited on the skin. The term "body fluids", as used herein, includes eccrine sweat, apocrine sweat, sebum, buildup of sensible moisture from transepidermal water loss, vaginal discharge, urine, and mixtures thereof. The term "body odor" as used herein means odors which are generated as a result of the natural functioning of a human or mammalian body. Such malodors include, but are not limited to malodors produced by microorganisms of the skin (i.e. bacterial decomposition of skin secretions), urine, or vaginal discharge, and mixtures thereof.

The term "skin" means human or mammalian skin. The term "entire body" means the entire external surface of human or mammalian skin. The term "vaginal malodor" relates specifically to those body malodors which emanate from the pelvic region of a woman, particularly the vagina and the panty line.

As used herein, the term "malodor" refers to the olfactory effect of compounds that is generally offensive or unpleasant to most people. Malodor includes olfactory effects such as the complex odors associated with body odor, mucus excrements, sweat, rot, feces, vomit or other bodily excrements or fluids. In the context of some embodiments of the present invention, malodor refers to unpleasant conceivable smell of certain amine-containing substances, such as, for example trimethylamine.

In the context of malodor, the terms "neutralize", "neutralizing" or "neutralization", refer to the ability of a compound or product to reduce or eliminate malodorous compounds, and thereby reduce or eliminate malodor originating therefrom. In the context of some embodiments of the present invention, malodor neutralization may be partial, affecting only some of the malodorous compounds in a given context, or affecting only part of a malodorous compound. A malodorous compound may be neutralized by chemical reaction resulting in a new chemical entity, by sequestration, by chelation, by association, or by any other interaction rendering the malodorous compound less malodorous or non-malodorous. Malodor neutralization may be distinguished from odor masking or odor blocking by a change in the malodorous compound, as opposed to a change in the ability to perceive the malodor without any corresponding change in the condition of the malodorous compound or substance. A genuine malodor neutralization provides a sensory and analytically measurable (e.g., by chemical assay or gas chromatograph) malodor reduction. Thus, if the malodor neutralizing composition delivers a genuine malodor neutralization, the composition will reduce malodors originating from certain malodorous compounds and substances.

As used herein, "odor blocking" refers to the ability of a compound to dull the human sense of smell. As used herein, "malodor masking" refers to the ability of a compound with a non-offensive or pleasant smell that is dosed such that it limits the ability to sense a malodorous compound. Malodor-masking may involve the selection of compounds which coordinate with an anticipated malodor to change the perception of the overall scent provided by the combination of odorous compounds. According to an aspect of embodiments of the present invention, there is provided a malodor neutralizing composition, which includes hyaluronic acid or a salt thereof (HA), N-acetyl cysteine or a pharmaceutically or cosmetically acceptable derivative thereof (NAC), and a pharmaceutically or cosmetically acceptable malodor neutralizing agent Ingredients of the Composition:

Hyaluronic Acid:

Hyaluronic acid (HA) is a naturally occurring high molecular weight polysaccharide that is found in many tissues of the body. Hyaluronic acid has been associated with maintaining moisture in the skin as well as with promoting wound healing and encouraging the formation of vessels. HA is known for its protective effect on skin irritations, and has been suggested as an agent for treating skin disease. HA is also known as a natural lubricant in internal organs and joints, when forming a gel that can lower the friction between two surfaces. As known in the art and shown in the Examples section that follows below, HA forms a more viscous gel at low (acidic) pH levels.

According to some embodiments of the present invention, the molecular weight of HA that is used in the composition ranges from about 5 kDa to about 20,000 kDa, or at least 1,000 kDa.

According to some embodiments of the present invention, a water-soluble salt of HA is used in the composition, such as sodium or potassium salt. In some embodiments, sodium salt of HA is used.

The amount of HA or a slat thereof in the composition ranges from 0.1% to 5%. Is some embodiments, the amount of HA in the composition is about 0.1%, 0.3%, 0.5%, 0.8%, 1%, 1.1%, 1.2%, 1.3%, 1.4%, 1.5%, 1.6%, 1.7%, 1.8%, 1.9%, 2.0%, 2.1%, 2.2%, 2.3%, 2.4%, 2.5%, 2.6%, 2.7%, 2.8%, 2.9%, 3.0%, 3.1%, 3.2%, 3.3%, 3.4%, 3.5%, 3.6%, 3.7%, 3.8%, 3.9%, 4.0%, 4.1%, 4.2%, 4.3%, 4.4%, 4.5%, 4.6%, 4.7%, 4.8%, 4.9% or 5.0%.

N-acetyl Cysteine or Derivatives and Analogs Thereof:

Acetylcysteine, N-acetyl cysteine, N-acetylcysteine or N-acetyl-L-cysteine are all referred to herein under the acronym "NAC". In some embodiments, the term "NAC" encompasses N-acetyl cysteine as well as to any pharmaceutically or cosmetically acceptable derivatives and analogs of N-acetyl cysteine that can be used in human and animal tissue. Derivatives and analogs of N-acetyl cysteine include L-cysteine, D-cysteine, N-acetyl-L-cysteine, N-acetyl-D-cysteine, NAC-amide, reduced glutathione, Nacystelyn (NAL; a lysine salt of NAC), S-Methyl-L-cysteine, γ-L-Glutamyl-L-cysteine, S-Allyl-D5-L-cysteine and S-Carboxymethyl-L-Cysteine (Carbocystein). In some embodiments, the term NAC refers to N-acetyl cysteine.

The amount of N-acetyl cysteine, or a derivative and an analog thereof, in the composition, ranges from 0.1% to 10% or from 0.1% to 5% by weight of the composition. Optionally, the concentration of NAC is about 0.1%, 0.3%, 0.5%, 0.8%, 1%, 1.1%, 1.2%, 1.3%, 1.4%, 1.5%, 1.6%, 1.7%, 1.8%, 1.9%, 2.0%, 2.1%, 2.2%, 2.3%, 2.4%, 2.5%, 2.6%, 2.7%, 2.8%, 2.9%, 3.0%, 3.1%, 3.2%, 3.3%, 3.4%, 3.5%, 3.6%, 3.7%, 3.8%, 3.9%, 4.0%, 4.1%, 4.2%, 4.3%, 4.4%, 4.5%, 4.6%, 4.7%, 4.8%, 4.9%, 5.0%, 6.0%, 7.0%, 8.0%, 9.0% or 10%.

Malodor Neutralizing Agent:

In the context of embodiments of the present invention, a malodor neutralizing agent is any substance that can effect malodor neutralization, as the term is defined herein. For example, in case where the malodorous compound is an amine-containing compound, any substance that can react with amines to produce a non-malodorous compound, and is cosmetically or pharmaceutically acceptable for topical use, is suitable as a malodor neutralizing agent. In some embodiments of the present invention, the malodor neutralizing composition includes at least one aldehyde. In some embodiments the aldehyde is also a fragrant; still, the composition is designed to effect malodor neutralization and not function merely by covering up or masking malodors.

The malodor control composition includes an aldehyde or a mixture of aldehydes that neutralize malodors in vapor and/or liquid phase via chemical reactions. Such aldehydes are also referred to herein as reactive aldehydes (RA). Aldehydes may react with amine-containing malodorous compounds following the path of Schiff-base formation. Aldehydes may also react with sulfur-containing malodorous compounds, forming thiol acetals, hemi thiolacetals, and thiol esters in vapor and/or liquid phase. In some embodiments, the malodor neutralizing composition includes reactive aldehydes that reduce amine malodors by 20% or more, or reduce thiol malodors by 20% or more.

It may be desirable for the reactive aldehydes used in the composition presented herein to be pharmaceutically and/or cosmetically acceptable for topical use, namely to have virtually no negative impact on the bodily part on which the composition is applied. In addition, it may be desirable for these reactive aldehydes to have virtually no negative impact on the desired scent of a product comprising the malodor neutralizing composition presented herein.

Exemplary aldehydes which may be used as a malodor neutralizing agent in a malodor neutralizing composition, according to some embodiments of the present invention, include, without limitation, Myrac aldehyde (4-(4-methyl-pent-3-enyl)cyclohex-3-ene-1-carbaldehyde), Lauric Aldehyde, Jasmal Aldehyde, Melonal Aldehyde, 2,4-Decadienal, 2,4-Dimethyl-3-cyclohexene carboxaldehyde, 2,4-dimethylbenzaldehyde, 2,4-hexadienal, 2,4-octadienal, 2,6,6-trimethyl-1-cyclohexene-1-acetaldehyde, 2,6-dimethyl 5-heptenal, 2,6-Nonadienal, 2-Dodecanal, 2-Ethylbutyraldehyde, 2-isopropyl-5-methyl-2-hexenal, 2-methyl butanal, 2-methyl butyraldehyde, 2-Methyl Valeraldehyde, 2-Methyl-2-pentenal, 2-methyl-3-(p-isopropylphenyl)-propionaldehyde, 2-methyl-3-tolylproionaldehyde, 2-methylpentenal, 2-pentyl-3-phenylpropenoic aldehyde, 2-phenyl-proprionaldehyde, 3-(p-isopropylphenyl)-propionaldehyde, 3,7-dimethyl-2,6-octadien-1-al), 3-Methyl-2-butenal, 3-methyl-4-phenyl propanal, 3-phenyl butanal, 3-phenyl-2-propenal, 3-phenylpropanal, 3-phenylpropionaldehyde, 4-dimethylbenzenepropanal, 4-ethyl benzaldehyde, Acalea (p-methyl-alpha-pentylcinnamaldehyde), acetaldehyde (ethanal), Adoxal (2,6,10-Trimethyl-9-undecenal), aldehyde C-11 MOA (2-methyl deca-1-al), aldehyde C12 MNA (2-methyl-1-undecanal), alpha-Amylcinnamic aldehyde, alpha-hexylcinnamaldehyde (2-hexyl 3-phenyl propenal), alpha-Methylcinnamaldehyde (2-methyl 3-pheny propenal), amylaldehyde, Anisaldehyde (p-methoxybenzene aldehyde), anisylpropanal 4-methoxy-alpha-methyl benzenepropanal (2-anisylidene propanal), Benzaldehyde, benzenepropanal (4-tert-butyl-alpha-methyl-hydrocinnamaldehyde), beta methyl Benzenepropanal, beta-cyclocitral, Bourgeonal (4-t-butylbenzenepropionaldehyde), butyraldehyde, Canthoxal, Catechaldehyde (3,4-dihydroxybenzaldehyde), Cinnamaldehyde (Cinnamic aldehyde), cis or trans-Heptenal, Citral, Citronellal (3,7-dimethyl 6-octenal), citronellal hydrate (7-hydroxy-3,7-dimethyl octan-1-al), Citronellyl oxyacetaldehyde, Corps 4322, Corps Iris, Cuminaldehyde (4-isopropyl benzaldehyde), Cyclal C (2,4-dimethyl-3-cyclohexen-1-carbaldehyde), cyclamen aldehyde, Cyclemax, Cyclocitral, Cyclosal, Cylcemone A (1,2,3,4,5,6,7,8-octahydro-8,8-dimethyl-2-naphthaldehyde), Cymal, Decanal, Decenal (2-,4-), Dihydrocitronellal (3,7-dimethyl octan-1-al), dimethyloctadienal, Dupical, Ethoxybenzaldehyde, Ethyl vanillin (3-ethoxy 4-hydroxybenzaldehyde), Floralozone, Florhydral (3-(3-Isopropyl-phenyl)-butyraldehyde), formyl Tricyclodecan, Geranial, Glutaraldehyde (Glutaric aldehyde), Helional (alpha-methyl-3,4-(methylenedioxy)-hydrocinnamaldehyde, Heliotropin (piperonal) 3,4-Methylene dioxy benzaldehyde, Heptenal, Hexenal (cis, trans, 2-, 3-), Hexyl Cinnamic aldehyde, hydrocinnamaldehyde, Hydrotropaldehyde, Hydroxycitronellal, Intreleven aldehyde (undec-10-en-1-al), Iso Cyclocitral (2,4,6-trimethyl-3-cyclohexene-1-carboxaldehyde), isobutyraldehyde, isovaleraldehyde (3-methyl butyraldehyde), Jasmonal H (alpha-n-hexyl-cinnamaldehyde), Jasmorange, Lauric aldehyde, Ligustral, Lilestralis 33 (2-methyl-4-t-butylphenyl)propanal), lilial, Lime aldehyde (Alpha-methyl-p-isopropyl phenyl propyl aldehyde), Lyral (4-(4-hydroxy-4-methyl pentyl)-3-cyclohexene-1-carboxaldehyde), lysmeral, Maceal, Mandarin aldehyde, Mefranal (3-methyl-5-phenyl pentanal), Melafleur (1,2,3,4,5,6,7,8-octahydro-8,8-dimethyl-2-naphthaldehyde), Melonal (2,6-Dimethyl-5-Heptenal), Methoxy Melonal (6-methoxy-2,6-dimethylheptanal), methoxycinnamaldehyde (trans-4-methoxycinnamaldehyde), Methyl Nonyl Acetaldehyde, Methyl Octyl Acetaldehyde, methylbutyraldehyde, methylcinnamaldehyde, Methylthiobutanal, Muguet aldehyde 50 (3,7-dimethyl-6-octenyl)oxyacetaldehyde), Myrac aldehyde isohexenyl cyclohexenyl-carboxaldehyde, Myrtenal (pin-2-ene-1-carbaldehyde), Neral, Nonanal, Nonenal (2-, 6-), Octanal, Octenal, Onicidal (2,6,10-trimethyl-5,9-undecadien-1-al), P.T. Bucinal, para-ethyl-alpha,alpha-dimethyl hydrocinnamaldehyde, pentanal, Pentanedial, Perillaldehyde L-4 (1-methylethenyl)-1-cyclohexene-1-carboxaldehyde), phenyl Butenal (2-phenyl 2-butenal), phenyl propenal, phenylacetaldehyde, Pino acetaldehyde, Precylcemone B (1-cyclohexene-1-carboxaldehyde), propionaldehyde (propanal), p-Tolylacetaldehyde (4-methylphenylacetaldehyde), pyruvaldehyde, Safranal (2,6,6-trimethyl-1,3-diene methanal), Salicylaldehyde (2-hydroxy benzaldehyde), satinaldehyde, Scentenal (octahydro-5-methoxy-4,7-Methano-1H-indene-2-carboxaldehyde), Syringaldehyde (3,5-dimethoxy 4-hydroxybenzaldehyde), tricyclodecylidenebutanal (4-Tricyclo5210-2, 6decylidene-8butanal), Tridecanal, Trifernal, Triplal, Trivertal (2,4-dimethyl-3-cyclohexene-1-carboxaldehyde), Undecenal (2-, 10-), valeraldehyde, Vanillin (4-methoxy 3-hydroxy benzaldehyde), Veratraldehyde (3,4-dimethoxybenzaldehyde), Vernaldehyde (1-Methyl-4-(4-methylpentyl)-3-cyclohexenecarbaldehyde), Vertocitral dimethyl tetrahydrobenzene aldehyde (2,4-dimethyl-3-cyclohexene-1-carboxaldehyde), and any combination or mixture thereof.

In some embodiments of the present invention, the aldehyde, used as a malodor neutralizing agent per-se, namely for its chemical reactivity with malodorous compounds, is selected so as not to impart a scent to the composition, thus the malodor neutralizing agent is a non-fragrant aldehyde.

In some embodiments, the aldehyde may be a fragrant aldehyde (perfume). Exemplary fragrant aldehydes which can be used as a malodor neutralizing agent include, without limitation, Myrac aldehyde, floral super, 2-ethoxy Benzylaldehyde, 2-isopropyl-5-methyl-2-hexenal, 5-methyl Furfural, 5-methyl-thiophene-carboxaldehyde, p-anisaldehyde, benzylaldehyde, cinnamic aldehyde, decyl aldehyde, Ligustral, Lyral, Melonal, o-anisaldehyde, P.T. Bucinal, thiophene carboxaldehyde, trans-4-decenal, trans 2,4-nonadienal, undecyl aldehyde, Helional (alpha-methyl-3,4-(methylenedioxy)-hydrocinnamaldehyde), Florhydral, Undecylenic Aldehyde, Adoxal (2,6,10-Trimethyl-9-undecenal), Bourgeonal (4-t-butylbenzenepropionaldehyde), Cymal, Florhydral (3-(3-isopropyl-phenyl)-butyraldehyde), Citronellal (3,7-dimethyl 6-octenal), Floralozone (para-ethyl-alpha,alpha-dimethyl hydrocinnamaldehyde), Floral Super, Pino Acetaldehyde, Styrax Coeur, Lauric Aldehyde, Jasmal Aldehyde, Melonal Aldehyde, lily aldehyde, trifernal, and any mixtures thereof.

In some embodiments, the malodor neutralizing composition includes a mixture of two, three, four or more aldehydes.

In some embodiments, the malodor control composition of the present invention may comprise, by total weight of the malodor neutralizing composition, from about 0.01% to about 30% by weight of aldehydes in the composition, or from about 0.1% to about 15% by weight of aldehydes, or from about 0.5% to about 10% by weight of aldehydes, or from about 0.1% to about 10% by weight of aldehydes in the composition.

According to some embodiments, the composition contains at least about 0.01%, 0.1%, 0.5%, 1%, 1.1%, 1.2%, 1.3%, 1.4%, 1.5%, 1.6%, 1.7%, 1.8%, 1.9%, 2.0%, 2.1%, 2.2%, 2.3%, 2.4%, 2.5%, 2.6%, 2.7%, 2.8%, 2.9%, 3.0%, 3.1%, 3.2%, 3.3%, 3.4%, 3.5%, 3.6%, 3.7%, 3.8%, 3.9%, 4.0%, 4.1%, 4.2%, 4.3%, 4.4%, 4.5%, 4.6%, 4.7%, 4.8%, 4.9% or 5.0% by weight of aldehydes. According to some embodiments, the composition contains less than about 0.01%, 0.1%, 0.5%, 1%, 1.1%, 1.2%, 1.3%, 1.4%, 1.5%, 1.6%, 1.7%, 1.8%, 1.9%, 2.0%, 2.1%, 2.2%, 2.3%, 2.4%, 2.5%, 2.6%, 2.7%, 2.8%, 2.9%, 3.0%, 3.1%, 3.2%, 3.3%, 3.4%, 3.5%, 3.6%, 3.7%, 3.8%, 3.9%, 4.0%, 4.1%, 4.2%, 4.3%, 4.4%, 4.5%, 4.6%, 4.7%, 4.8%, 4.9% or 5.0% by weight of aldehydes.

pH Adjusting Agent:

In some embodiments of the present invention, the composition is characterized by an acidic pH level. The acidic pH is beneficial in promoting neutralization of malodorous compounds, and in some embodiments the acidic nature of the composition is beneficial for use on mucus membrane such as vaginal areas. The low pH also contributes to the mechanical characteristics of the composition, by keeping the HA gel's viscosity relatively high, at a range of about 5 to 30 Pa·s.

NAC and derivatives thereof are acidic by nature and can be used to set the pH of the composition to the desired level. Other pH adjusting agents useful in the context of the present invention include acids and buffers as these are known in the art.

The composition of the present invention includes a buffering agent which may be carboxylic acid, or a dicarboxylic acid (e.g., maleic acid). The acid is used in the composition for maintaining the desired pH.

Buffering agents and pH adjusting agents suitable for the desired pH of the malodor neutralizing composition presented herein include, without limitation, acetate, glycine-HCl, cacodylate, citrate, phosphate-citrate MES, PBS, TBS, TNT, PBT and the likes, as these acidic buffers and pH adjusting agents are known in the art.

Other suitable buffering agents useful for setting the desired pH in the compositions of the present invention include biological buffering agents such as nitrogen-containing materials, sulfonic acid buffers like 3-(N-morpholino)propanesulfonic acid (MOPS) or N-(2-Acetamido)-2-aminoethanesulfonic acid (ACES), lysine or lower alcohol amines like mono-, di-, and tri-ethanolamine, TRIS, 2-amino-2-ethyl-1,3-propane diol, 2-amino-2-methyl-propanol, 2-amino-2-methyl-1,3-propanol, disodium glutamate, N-methyl diethanolamide, 2-dimethylamino-2-methylpropanol (DMAMP), 1,3-bis(methylamine)-cyclohexane, 1,3-diamino-propanol N,N'-tetra-methyl-1,3-diamino-2-propanol, N,N-bis(2-hydroxyethyl)glycine (bicine) and N-tris (hydroxymethyl)methyl glycine (tricine). Mixtures of any of the above are also contemplated.

The malodor neutralizing compositions may contain at least about 0%, at least about 0.001%, at least about 0.01%, by weight of the composition, of a buffering agent. The composition may also contain no more than about 1%, no more than about 0.75%, no more than about 0.5%, by weight of the composition, of a buffering agent.

The malodor neutralizing composition presented herein may have a pH ranging from about 3 to about 6, from about 4 to about 6, or from about 5 to about 6. In some embodiments, the pH of the composition is set to be lower than 6, or lower than 5.5, or lower than 5, or lower than 4.5. In some embodiments, the pH of the composition is about 6, 5.5, 5, 4.5, 4, 3.5 or about 3.

Water:

Water is present in any amount for the composition to make a fluid liquid, a viscous liquid, a gel or any other form of an aqueous solution. In some embodiments, water may be present in an amount of about 50% to 99.5%, alternatively about 90% to about 99.5%, alternatively about 92% to about 99.5%, alternatively about 95%, by weight of said malodor neutralizing composition.

Exemplary Composition:

According to an aspect of some embodiments of the present invention, the malodor neutralizing composition consists of hyaluronic acid sodium salt (HA), N-acetylcysteine (NAC) and an aldehyde, wherein NAC is used to set the pH, typically but not exclusively, to below 6.5 or below 6. Such a composition is formulated to be minimal and provide just the malodor neutralizing effect while exerting minimal side-effects or other unintentional effects to the user.

In some embodiments of this aspect, the amount (concentration) of hyaluronic acid sodium salt ranges from 0.1% to 5% by weight of the total weight of the composition. In some embodiments, the concentration of hyaluronic acid sodium salt is 1% or 2%.

In some embodiments of this aspect, the amount (concentration) of N-acetylcysteine ranges from 0.1% to 10% by weight of the total weight of the composition. In some embodiments, the concentration of N-acetylcysteine is 1%, 2%, 5% or 10%.

In some embodiments of this aspect, the amount (concentration) of aldehyde ranges from about 0.1% to about 10% by weight of the total weight of the composition.

In some embodiments, the concentration of aldehyde is about 1%, 5% or 10%.

According to another aspect of some embodiments of the present invention, there is provided a malodor neutralizing composition that includes:
a) hyaluronic acid sodium salt;
b) N-acetylcysteine;
c) myrac aldehyde; and
d) water,
and having a pH equal or lower than 6.

In some embodiments, the amount (concentration) of hyaluronic acid sodium salt ranges from 0.1% to 5% by weight of the total weight of the composition. In some embodiments, the concentration of hyaluronic acid sodium salt is 1% or 2%.

In some embodiments, the amount (concentration) of N-acetylcysteine ranges from 0.1% to 10% by weight of the total weight of the composition. In some embodiments, the concentration of N-acetylcysteine is 1%, 2%, 5% or 10%.

In some embodiments, the amount (concentration) of myrac aldehyde ranges from about 0.1% to about 10% by weight of the total weight of the composition. In some embodiments, the concentration of myrac aldehyde is about 1%, 5% or 10%.

Optional Ingredients of the Composition:
Fragrances and Perfumes:

Fragrances and perfumes constitute an optional component of the composition according to some embodiment of the present invention, generally referred to as a scented composition. Fragrances and perfumes can be included in the composition at a level which is non-irritating to the ordinary user's mucus membrane or dry skin and/or respiratory tract, yet is discernible by the human sense of smell either before and/or after application of the scented composition to the mucus membrane or dry skin. The scented composition is concocted so as to be safe for use on mucus membrane and skin.

The fragrant component in scented compositions can be in the form of a free fragrance (not encapsulated), in the form of encapsulated fragrance, or mixtures thereof. The fragrance is typically present in a scented composition at a level of from about 0.01% to about 20% by weight of the scented malodor neutralizing composition.

In some embodiments, the free fragrance may be diluted in a solvent to aid in incorporation into the scented malodor neutralizing compositions provided herein. Suitable solvents found in the Cosmetic Bench Reference, 1994 Edition, page 54, which is incorporated herein by reference. Free fragrance may be composed of conventional perfume ingredients at a level of from about 0.01% to about 5%, or from about 0.05% to about 3%, or from about 0.05% to about 2%, or from about 0.1% to about 1%, by weight of the malodor neutralizing composition.

Non-limiting examples of fragrance include 2-decenal, 3,7-dimethyloctanal, 4-terpinenol, 4-tert-butylcyclohexyl formate, allo-ocimene, allyl caproate, allyl cyclohexaneacetate, allyl cyclohexanepropionate, allyl heptanoate, alpha-ionone, alpha-irone, alpha-iso "gamma" methyl ionone, alpha-pinene, alpha-terpinene, amyl acetate, amyl benzoate, amyl propionate, anethol, anisic aldehyde, anisole, benzaldehyde, benzyl acetate, benzyl acetone, benzyl alcohol, benzyl butyrate, benzyl formate, benzyl iso valerate, benzyl propionate, beta gamma hexenol, beta-caryophyllene, beta-damascone, beta-ionone, beta-pinene, butyl benzoate, butyl caproate, camphene, camphor gum, carvacrol, cinnamic alcohol, cinnamyl formate, cis-3-hexenyl acetate, cis-3-hexenyl butyrate, cis-3-hexenyl caproate, cis-3-hexenyl tiglate, cis-3-hexenyl valerate, cis-jasmone, citral (neral), citronellol, citronellyl acetate, citronellyl formate, citronellyl isobutyrate, citronellyl nitrile, citronellyl oxyacetaldehyde, citronellyl propionate, cuminic alcohol, cuminic aldehyde, Cyclal C, cyclohexyl ethyl acetate, d-carvone, decyl aldehyde, delta-undecalactone, dihydro myrcenol, dihydromyrcenyl acetate, dimethyl benzyl carbinol, dimethyl benzyl carbinyl acetate, dimethyl benzyl carbinyl propionate, dimethyl octanol, dimethyl phenylethyl carbinyl acetate, diphenyl methane, diphenyl oxide, d-limonene, dodecalactone, ethyl acetate, ethyl aceto acetate, ethyl amyl ketone, ethyl benzoate, ethyl butyrate, ethyl hexyl ketone, ethyl methyl phenyl glycidate, ethyl phenyl acetate, eucalyptol, eugenol, fenchyl acetate, fenchyl alcohol, flor acetate (tricyclo decenyl acetate), frutene (tricyclo decenyl propionate), gamma methyl ionone, gamma-ionone, gamma-n-methyl ionone, gamma-nonalactone, gamma-terpinene, gamma-undecalactone, geraniol, geranyl acetate, geranyl acetoacetate, geranyl butyrate, geranyl formate, geranyl isobutyrate, geranyl nitrile, geranyl propionate, heliotropine, heptyl acetate, heptyl isobutyrate, heptyl propionate, hexenol, hexenyl acetate, hexenyl isobutyrate, hexyl acetate, hexyl formate, hexyl isobutyrate, hexyl isovalerate, hexyl neopentanoate, hexyl tiglate, hydratropic alcohol, hydroxycitronellal, indole, isoamyl alcohol, isobornyl acetate, isobornyl propionate, isobutyl benzoate, isobutyl caproate, isobutyl quinoline, isomenthol, isomenthone, isononyl acetate, isononyl alcohol, isopulegol, isopulegyl acetate, isoquinoline, laevo-carveol, laevo-carvone, lauric aldehyde (dodecanal), lavandulyl acetate, ligustral, Lilial (p-t-Bucinal), linalool, linalool oxide, linalyl acetate, linalyl butyrate, linalyl formate, linalyl isobutyrate, linalyl propionate, menthone, menthyl acetate, methyl acetophenone, methyl amyl ketone, methyl anthranilate, methyl benzoate, methyl benzyl acetate, methyl chavicol, methyl eugenol, methyl heptenone, methyl heptine carbonate, methyl heptyl ketone, methyl hexyl ketone, methyl nonyl acetaldehyde, methyl octyl acetaldehyde, methyl octyl ketone, methyl phenyl carbinyl acetate, methyl salicylate, methyl-N-methyl anthranilate, myrcene, myrcenyl acetate, neral, nerol, neryl acetate, nonalactone, nonyl acetate, nonyl alcohol, nonyl aldehyde, nonyl butyrate, octalactone, octyl acetate, octyl alcohol (octanol-2), octyl aldehyde, orange terpenes (d-limonene), para-cresol, para-cresyl methyl ether, para-cymene, para-isopropyl para-methyl acetophenone, para-methoxy acetophenone, phenethyl anthranilate, phenethyl butyrate, phenoxy ethanol, phenoxy ethyl proprionate, phenyl acetaldehyde, phenyl ethyl acetate, phenyl ethyl alcohol, phenyl ethyl dimethyl carbinol, phenyl heptanol, phenyl hexanol, prenyl acetate, propyl butyrate, pulegone, rose oxide, safrole, terpineol, terpinolene, terpinyl acetate, terpinyl propionate, tetrahydro linalool, tetrahydro myrcenol, thymol, undecanal, undecyl alcohol, Veratrol, Verdox, Vertenex, viridine, and any mixture thereof.

The use of small amounts of fragrance ingredients that have low odor detection threshold values can improve perfume odor character, even though they are not highly volatile. The phrase "odor detection threshold" of an odorous material means the lowest vapor concentration of that material which can be olfactorily detected. The odor detection threshold and some odor detection threshold values are discussed in, e.g., "Standardized Human Olfactory Thresholds", M. Devos et al, IRL Press at Oxford University Press, 1990; and "Compilation of Odor and Taste Threshold Values Data", F. A. Fazzalari, editor, ASTM Data Series DS 48A, American Society for Testing and Materials, 1978, both publications being incorporated by reference.

Fragrances that have a significantly low odor detection threshold useful herein, are selected from the group consisting of ambrox dl, bacdanol, benzyl salicylate, calone, cetalox, cis-3-hexenyl salicylate, cymal, ebanol, ethyl anthranilate, ethyl methyl phenyl glycidate, ethyl vanillin, dihydro iso jasmonate, gamma dodecalactone, flor acetate, florhydral, frutene, heliotropine, alpha ionone, beta ionone, iso eugenol, alpha isomethylionone, lilial, lyral, methyl dihydrojasmonate, methyl beta naphthyl ketone, beta naphthol methyl ether, para hydroxy phenyl butanone, undecalactone gamma, vanillin, and mixtures thereof. These fragrances are preferably present at low levels in addition to more volatile fragrances, typically less than about 20%, preferably less than about 15%, more preferably less than about 10%, by weight of the scented composition.

fragrance ingredients that have a significantly low odor detection thresholds which are useful herein, include allyl amyl glycolate, anethol, benzyl acetone, butyl anthranilate, cinnamic alcohol, cyclal C, cyclogalbanate, 4-decenal, ethyl-2-methyl butyrate, eugenol, damascenone, alpha damascone, fructone, herbavert, indole, iso cyclo citral, keone, linalool, methyl anthranilate, methyl heptine carbonate, methyl isobutenyl tetrahydropyran, methyl nonyl ketone, nerol, para anisic aldehyde, phenyl acetaldehyde, undecylenic aldehyde and any combination thereof.

It is noted herein that some fragrances can have a dual role in the malodor neutralizing composition, wherein the fragrance neutralizes the malodorous substance and masks its malodor. For example, some aldehydes are characterized by a notable pleasant perfume scent, and in addition to produce a fragrant scent, these aldehydes can react with amine-containing malodorous substance, thereby neutralizing the malodorous substance.

In some embodiments, the malodor neutralizing agent is also a fragrance. In some embodiments, the malodor neutralizing agent is an aldehyde that is also a fragrance. In other embodiments, the malodor neutralizing agent is not a fragrance.

Antimicrobial Compounds:

The malodor neutralizing composition of the present invention may include an effective amount of an antimicrobial agent for reducing microbes in the treated areas.

Antimicrobial compounds are effective on gram negative and gram positive bacteria and fungi typically found on mucus membrane and skin. In some embodiments, the antimicrobial agent is selected for inhibiting the growths and proliferation, reducing or eliminating microbial species that are known to cause malodor in mucus membranes and occluded skin areas, which include, without limitation, *Trichomonia vaginalis*, Vaginal Thrush or Vulvovaginal Candidiasis (VVC), *Prevotella* sp., *Mobiluncus* sp., *G. vaginalis* and *Mycoplasma hominis*. Other microbial species which can be targeted by the additional antimicrobial agent include, without limitation, *Klebsiella pneumoniae, Staphylococcus aureus, Aspergillus niger, Klebsiella pneumoniae, Steptococcus pyogenes, Salmonella choleraesuis, Escherichia coli, Trichophyton mentagrophytes*, and *Pseudomonoas aeruginosa*. In some embodiments, the antimicrobial compounds are also effective on viruses such H1-N1, Rhinovirus, Respiratory Syncytial, Poliovirus Type 1, Rotavirus, Influenza A, Herpes simplex types 1 & 2, Hepatitis A, and Human Coronavirus.

Antimicrobial compounds suitable in the malodor neutralizing composition of the present invention are pharmaceutically accepted for topical use, and include organic sulfur compounds, halogenated compounds, cyclic organic nitrogen compounds, low molecular weight aldehydes, quaternary compounds, dehydroacetic acid, phenyl and phenoxy compounds, or mixtures thereof.

In some embodiments, the antimicrobial agent may be present in an amount from about 500 ppm to about 7000 ppm, alternatively about 1000 ppm to about 5000 ppm, alternatively about 1000 ppm to about 3000 ppm, alternatively about 1400 ppm to about 2500 ppm, by weight of the malodor neutralizing composition.

Preservatives:

The malodor neutralizing composition of the present invention may include a preservative. The preservative is included in the present invention in an amount sufficient to prevent spoilage or prevent growth of inadvertently added microorganisms for a specific period of time, but not sufficient enough to contribute to the odor neutralizing performance of the malodor neutralizing composition. In other words, the preservative is not being used as the antimicrobial compound to kill microorganisms on the surface onto which the composition is deposited in order to eliminate odors produced by microorganisms. Instead, it is being used to prevent spoilage of the malodor neutralizing composition in order to increase the shell-life of the composition.

The preservative can be any organic preservative material which is pharmaceutically or cosmetically acceptable for topical use. Suitable preservatives include organic sulfur compounds, halogenated compounds, cyclic organic nitrogen compounds, low molecular weight aldehydes, parabens, propane diaol materials, isothiazolinones, quaternary compounds, benzoates, low molecular weight alcohols, dehydroacetic acid, phenyl and phenoxy compounds, or mixtures thereof.

Suitable levels of preservative range from about 0.0001% to about 0.5%, or from about 0.0002% to about 0.2%, or from about 0.0003% to about 0.1%, by weight of the malodor neutralizing composition.

Skin Aids:

The compositions of the present invention also optionally include skin aids. The term "skin aids", as used herein, refers to skin protectants, emollients, and moisturizers.

Skin protectants useful in the present invention are found in the Cosmetic Bench Reference, 1994 Edition, page 53; and the Monograph on Skin Protectant Drug Products for Over-the-Counter Human Use, 21 CFR 347. Exemplary skin protectants include corn starch, kaolin, mineral oil, sodium bicarbonate, dimethicone, zinc oxide, colloidal oatmeal, and mixtures thereof. When present, the skin protectants comprise from about 0.1% to about 80%, or from about 0.1% to about 30%, or from about 0.1% to about 10%, by weight of the composition.

Emollients and moisturizers can be found in the Cosmetic Bench Reference, 1994 Edition, pages 27-32 and 46-48, incorporated herein by reference. Exemplary emollients and moisturizers include tocopherol, tocopheryl acetate, aloe, vegetable oils, mineral oil, petrolatum, jojoba oil, and mixtures thereof. In some embodiments, the emollients and moisturizers are encapsulated or spray/freeze dried. Examples of preferred commercial spray/freeze dried aloe useful in some embodiments of the present invention include Terra-Dry™ Freeze Dried Aloe, Terra-Pure™ Freeze or Spray Dried Aloe, and Terra-Spray™ Spray Dried Aloe, all from Terry Laboratories. When present, the skin aids comprise from about 0.1% to about 50%, or from about 0.1% to about 25%, or from about 0.1% to about 10%, by weight of the composition.

Lubricants:

In some embodiments of the present invention, the compositions may optionally comprise additional agents which provide enhanced slip/lubrication characteristics for reduced skin to skin friction between intertriginous skin sites. Such slip/lubrication agents include polyethylene; nylon; polytetrafluoroethylene; silica which is in the form of microspheres, ellipsoids, barrel-shapes, and the like; mica, silicone (e.g. dimethicone) and metallic stearates (e.g. zinc stearate); and mixtures thereof.

Anti-pruritic Agents:

In some embodiments of the present invention, the compositions may optionally comprise anti-pruritic agents such as those known in the art. Examples of anti-pruritic agents include magnesium-L-Lactate, hydrocortisone, hydrocortisone acetate, and colloidal oatmeal. A description of anti-pruritic agents are found in the Handbook of Non Prescription Drugs, 10th Edition, p. 529, 1993; which is incorporated herein by reference. When included in the composition, anti-pruritic agents may be present from about 0.1% to about 40%, by weight of the composition.

Colorants:

In some embodiments of the present invention, the compositions may optionally comprise colorants such as those known in the art. Colorants and dyes can be optionally added to the malodor neutralizing compositions of the present invention for visual appeal and performance impression. Colorants suitable for use in the present invention are found in the Cosmetic Bench Reference, 1994 Edition, pages 21-22, which is incorporated herein by reference.

Diluents:

The malodor neutralizing composition of the present invention may be combined with one or more diluents. When combined with said diluents, the malodor neutralizing composition may comprise from about 0.1 to about 80% or from about 1% to about 50% or from about 10% to about 30% of the composition. For use in the present invention, diluents with low scent intensity are preferred, but not required. Exemplary diluents include DBE-LVP (Mixed aliphatic ester fluid (CAS #1119-40-0 and CAS #627-93-0 from INVISTA), dipropylene glycol methyl ether, 3-methoxy-3-methyl-1-butanol, isononyl acetate, benzyl alcohol, florol, dioctyl adipate (CAS #123-79-5), Tripropylene glycol Methyl ether (CAS #25498-49-1), Dow Corning 200® Fluid, 1.5 CST®. (from the Dow Corning Co.), Dipropylene glycol n-propyl ether, Xiameter® PMX-200 Silicone Fluid 1.5CS® (from the Dow Corning Co.), cellulose, Ethyl ether and mixtures thereof.

Surfactants, Wetting Agents and Humectants:

Surfactants, humectants, wetting agents and low molecular weight monohydric alcohols, e.g., ethanol, methanol, and isopropanol, or polyols, such as ethylene glycol and propylene glycol, can also be useful additives in the compositions presented herein. Non-limiting examples of wetting agents include block copolymers of ethylene oxide and propylene oxide. Suitable block polyoxyethylene-polyoxypropylene polymeric surfactants include those based on ethylene glycol, propylene glycol, glycerol, trimethylolpropane and ethylenediamine.

Drug-delivery Formulations:

According to some embodiments of the present invention, a malodor neutralizing composition as described herein can be formulated to deliver one or more bioactive agent to the treated area, and thus the composition further comprises one or more bioactive agent(s). In some embodiments, such drug-delivery compositions are formed such that the bioactive agent is released therefrom upon contacting a mucus membrane or an occluded skin area. Thus, the composition, according to some embodiments of the present invention, can be used to neutralize malodor, as discussed herein, while at the same time serve as a reservoir and vehicle for delivering a bioactive agent to the treated area.

It is noted herein that while the incorporation of a bioactive agent in the composition may affect the characteristics thereof, the composition is designed to possess desired properties presented hereinabove while adding the capacity of delivering bioactive agent(s) as discussed hereinbelow.

As used herein, the phrase "bioactive agent" describes a molecule, compound, complex, adduct and/or composite that exerts one or more biological and/or pharmaceutical activities. The bioactive agent can thus be used, for example, to relieve pain, prevent inflammation, prevent and/or reduce and/or eradicate an infection, promote wound healing, promote tissue regeneration, effect tumor/metastasis eradication/suppression, effect local immune-system suppression, and/or to prevent, ameliorate or treat various medical conditions.

"Bioactive agents", "pharmaceutically active agents", "pharmaceutically active materials", "pharmaceuticals", "therapeutic active agents", "biologically active agents", "therapeutic agents", "medicine", "medicament", "drugs" and other related terms may be used herein interchangeably, and all of which are meant to be encompassed by the term "bioactive agent".

The term "bioactive agent" in the context of the present invention also includes diagnostic agents, including, for example, chromogenic, fluorescent, luminescent, phosphorescent agents used for marking, tracing, imaging and identifying various biological elements such as small and macromolecules, cells, tissue and organs; as well as radioactive materials which can serve for both radiotherapy and tracing, for destroying harmful tissues such as tumors/metastases in the local area, or to inhibit growth of healthy tissues, such as in current stent applications; or as biomarkers for use in nuclear medicine and radio-imaging.

Bioactive agents useful in accordance with the present invention may be used singly or in combination, namely more than one type of bioactive agents may be used together in one composition, and therefore be released simultaneously from the composition.

In some embodiments, the concentration of a bioactive agent in the formulation ranges from 0.001% by weight to 10% by weight of the total weight of the composition, and even more in some embodiments. Higher and lower values of the content of the bioactive agent are also contemplated, depending on the nature of the bioactive agent used and the intended use of the composition.

When using the term "bioactive agent" in the context of releasing or eluting a bioactive agent, it is meant that the bioactive agent is substantially active upon its release.

As discussed hereinbelow, the bioactive agent may have an influence on the composition by virtue of its own reactivity with one or more of the composition components, or by virtue of its chemical and/or physical properties per-se. It is therefore noted that in general, the bioactive agent is selected suitable for being incorporated in the composition such that it can elute from the composition in the intended effective amount and release rate, while allowing the composition to exhibit the desired properties, as discussed herein, namely neutralize malodors.

A bioactive agent, according to some embodiments of the present invention, can be, for example, a macro-biomolecule or a small, organic molecule.

According to some embodiments of the present invention, the bioactive agent is a non-proteinous substance, namely a substance possessing no more than four amino acid residues in its structure.

According to some embodiments of the present invention, the bioactive agent is a non-carbohydrate substance, namely a substance possessing no more than four sugar (aminoglycoside inclusive) moieties in its structure.

According to some embodiments of the present invention, the bioactive agent is substantially devoid of reactive functional groups such as primary amines, disulfides, and sulfhydroxyl group. In some embodiments, the bioactive agent is not a malodorous substance.

The term "macro-biomolecules" as used herein, refers to a polymeric biochemical substance, or biopolymers, that occur naturally in living organisms. Amino acids and nucleic acids are some of the most important building blocks of polymeric macro-biomolecules, therefore macro-biomolecules are typically comprised of one or more chains of polymerized amino acids, polymerized nucleic acids, polymerized saccharides, polymerized lipids and combinations thereof. Macromolecules may comprise a complex of several macromolecular subunits which may be covalently or non-covalently attached to one another. Hence, a ribosome, a cell organelle and even an intact virus can be regarded as a macro-biomolecule. A macro-biomolecule, as used herein, has a molecular weight higher than 1000 dalton (Da), and can be higher than 3000 Da, higher than 5000 Da, higher than 10 kDa and even higher than 50 KDa. Representative examples of macro-biomolecules, which can be beneficially incorporated in the composition described herein include, without limitation, peptides, polypeptides, proteins, enzymes, antibodies, oligonucleotides and labeled oligonucleotides, nucleic acid constructs, DNA, RNA, antisense, polysaccharides, viruses and any combination thereof, as well as cells, including intact cells or other sub-cellular components and cell fragments.

As used herein, the phrase "small organic molecule" or "small organic compound" refers to small compounds which consist primarily of carbon and hydrogen, along with nitrogen, oxygen, phosphorus and sulfur and other elements at a lower rate of occurrence. In the context of the present invention, the term "small" with respect to a compound, agent or molecule, refers to a molecular weight lower than about 1000 grams per mole. Hence, a small organic molecule has a molecular weight lower than 1000 Da, lower than 500 Da, lower than 300 Da, or lower than 100 Da.

Representative examples of small organic molecules, that can be beneficially incorporated in the composition described herein include, without limitation, angiogenesis-promoters, cytokines, chemokines, chemo-attractants, chemo-repellants, drugs, agonists, amino acids, antagonists, anti-histamines, antibiotics, antigens, antidepressants, antihypertensive agents, analgesic and anesthetic agents, anti-inflammatory agents, antioxidants, anti-proliferative agents, immunosuppressive agents, clotting factors, osseointegration agents, anti-viral agents, chemotherapeutic agents, co-factors, fatty acids, growth factors, haptens, hormones, inhibitors, ligands, saccharides, radioisotopes, radiopharmaceuticals, steroids, toxins, vitamins, minerals and any combination thereof.

Representative examples of bioactive agents suitable for use in the context of the present embodiments include, without limitation, analgesic, anesthetic agents, antibiotics, antitumor and chemotherapy agents, agonists and antagonists agents, amino acids, angiogenesis-promoters, anorexics, antiallergics, antiarthritics, antiasthmatic agents, antibodies, anticholinergics, anticonvulsants, antidepressants, antidiabetic agents, antidiarrheals, antifungals, antigens, antihistamines, antihypertensive agents, antiinflammatory agents, antimigraine agents, antinauseants, antineoplastics, antioxidants, antiparkinsonism drugs, antiproliferative agents, antiprotozoans, antipruritics, antipsychotics, antipyretics, antisenses nucleic acid constructs, antispasmodics, antiviral agents, bile acids, calcium channel blockers, cardiovascular preparations, cells, central nervous system stimulants, chemo-attractants, chemokines, chemo-repellants, chemotherapeutic agents, cholesterol, co-factors, contraceptives, cytokines, decongestants, diuretics, DNA, Drugs and therapeutic agents, enzyme inhibitors, enzymes, fatty acids, glycolipids, growth factors, growth hormones, haemostatic and antihemorrhagic agents, haptens, hormone inhibitors, hormones, hypnotics, immunoactive agents, immunosuppressive agents, inhibitors and ligands, labeled oligonucleotides, microbicides, muscle relaxants, nucleic acid constructs, oligonucleotides, parasympatholytics, peptides, peripheral and cerebral vasodilators, phospholipids, polysaccharides, proteins, psychostimulants, radioisotopes, radiopharmaceuticals, receptor agonists, RNA, saccharides, saponins, sedatives, small organic molecules, spermicides, steroids, sympathomimetics, toxins, tranquilizers, vaccines, vasodilating agents, viral components, viral vectors, viruses, vitamins, and any combination thereof.

The bioactive agent may be selected to achieve either a local or a systemic response. The bioactive agent may be any prophylactic agent or therapeutic agent suitable for various topical, enteral and parenteral types of administration routes including, but not limited to sub- or trans-cutaneous, intradermal transdermal, transmucosal, intramuscular administration and mucosal administration.

One class of bioactive agents which can be incorporated in the composition, according to some embodiments of the present invention, is the class of analgesic agents that alleviate pain e.g. NSAIDs, COX-2 inhibitors, opiates and morphinomimetics.

Spermicides, or spermicidal agents, is another class of bioactive agents which can be incorporated, for example, in a composition intended for use in the female genital organs, according to some embodiments of the present invention, as well as an optional ingredient in the malodor neutralizing composition presented herein, which include, without limitation, nonoxynol-9, octoxynol-9, benzalkonium chloride and menfegol.

Another class of bioactive agents which can be incorporated in the composition, according to some embodiments of the present invention, is the class of anesthetic agents. Another class of bioactive agents which can be incorporated in the composition, according to some embodiments of the present invention, is the class of therapeutic agents that promote angiogenesis. Non-limiting examples include growth factors, cytokines, chemokines, steroids cell survival and proliferation agents.

Another class of bioactive agents which can be incorporated in the composition, according to some embodiments of the present invention, especially in certain embodiments wherein tissue regeneration is desirable, and application involving implantable devices and tissue healing, are cytokines, chemokines and related factors.

Non-limiting examples of immunosuppressive drugs or agents, commonly referred to herein as immunosupressants, include glucocorticoids, cytostatics, antibodies, drugs acting on immunophilins and other immunosupressants.

Non-limiting examples of haemostatic agents include kaolin, smectite and tranexamic acid.

It is noted herein that kaolin is an exemplary bioactive agent which has a limited solubility in the composition, and is therefore added in the form of a dry powder, and thus acts, at least to some extent, also as a filler in the composition. This dual function, bioactive agent and filler, may characterize any additive or bioactive agent which are encompassed by embodiments of the present invention and are contemplated therewith.

Additional bioactive agents which can be beneficially incorporated in the composition, according to some embodiments of the present invention, include cytotoxic factors or cell cycle inhibitors and other agents useful for interfering with cell proliferation.

Additional bioactive agents which can be beneficially incorporated in the composition, according to some embodiments of the present invention, include genetic therapeutic agents and proteins, such as ribozymes, anti-sense polynucleotides and polynucleotides coding for a specific product (including recombinant nucleic acids) such as genomic DNA, cDNA, or RNA. The polynucleotide can be provided in "naked" form or in connection with vector systems that enhances uptake and expression of polynucleotides. These can include DNA compacting agents (such as histones), non-infectious vectors (such as plasmids, lipids, liposomes, cationic polymers and cationic lipids) and viral vectors such as viruses and virus-like particles (i.e., synthetic particles made to act like viruses). The vector may further have attached peptide targeting sequences, anti-sense nucleic acids (DNA and RNA), and DNA chimeras which include gene sequences encoding for ferry proteins such as membrane translocating sequences ("MTS"), tRNA or rRNA to replace defective or deficient endogenous molecules and herpes simplex virus-1 ("VP22").

Additional bioactive agents which can be beneficially incorporated in the composition, according to some embodiments of the present invention, include gene delivery agents, which may be either endogenously or exogenously controlled.

Additional bioactive agents which can be beneficially incorporated in the composition, according to some embodiments of the present invention, include the family of bone morphogenic proteins ("BMP's") as dimers, homodimers, heterodimers, or combinations thereof, alone or together with other molecules. Alternatively or, in addition, molecules capable of inducing an upstream or downstream effect of a BMP can be provided. Such molecules include any of the "hedgehog" proteins, or the DNA's encoding them.

Additional bioactive agents which can be beneficially incorporated in the composition, according to some embodiments of the present invention, include chemotherapeutic agents. Additional bioactive agents which can be beneficially incorporated in the composition, according to some embodiments of the present invention, include antibiotic agents.

Antiviral agents may include nucleoside phosphonates and other nucleoside analogs, AICAR (5-amino-4-imidazolecarboxamide ribonucleotide) analogs, glycolytic pathway inhibitors, glycerides, anionic polymers, and the like.

Additional bioactive agents which can be beneficially incorporated in the composition, according to some embodiments of the present invention, include viral and non-viral vectors.

Additional bioactive agents which can be beneficially incorporated in the composition, according to some embodiments of the present invention, include steroidal anti-inflammatory drugs. Additional bioactive agents which can be beneficially incorporated in the composition, according to some embodiments of the present invention, include antioxidants.

Additional bioactive agents which can be beneficially incorporated in the composition, according to some embodiments of the present invention, include vitamins.

Additional bioactive agents which can be beneficially incorporated in the composition, according to some embodiments of the present invention, include hormones.

Additional bioactive agents which can be beneficially incorporated in the composition, according to some embodiments of the present invention, include cells of human origin (autologous or allogeneic), including stem cells, or from an animal source (xenogeneic), which can be genetically engineered if desired to deliver proteins of interest.

Modes of Applying the Compositions:

In some embodiments of the present invention, the malodor neutralizing compositions are to be applied directly to the skin or mucus membranes. Various applicators are useful for delivering the compositions to various areas of the body for optimal malodor control. For example, the compositions are optionally deposited in a bottle, a canister, a spray dispenser, a manually activated spray dispenser, or on a wipe structure which later is contacted with the body to transfer the composition to the designated area. Bottles and canisters known in the art are suitable for use in delivering the compositions of the present invention. Bottles and canisters preferably comprise lids with small apertures for convenient dispensing of the composition.

The composition of the present invention can also be delivered as a liquid, gel, emulsion or suspension via a spray dispenser or a bottle, such that when applied or sprayed onto the skin. An optional propellant solvent can be present in the composition to assist in propelling the composition out from the container and for better skin coverage. The propellant can be selected so as to dry/volatilize off to leave a film of the composition on the skin. Examples of such configurations include aerosols, liquid sprays or gel sprays. In some embodiments, the composition is applied by means of a manually activated spray dispenser which delivers the composition as a liquid or gel without the use of propellants. Spray dispensers useful herein are described more fully in U.S. Pat. Nos. 2,450,205 and 2,840,277, both of which are incorporated herein by reference in their entireties.

In some embodiments, the composition is applied by means of a wipe. Any wipe structures and/or methods of making the wipe structures commonly known in the art may be used. The wipe comprises a flexible dispensing means which include papers, cloths, non-wovens, films, foams, sponges, rollers, pads, tissues, cotton balls, and the like. Suitable wipe substrates comprise a porous material, such as the non-woven substrates, foams, or sponges, which are capable of holding the composition within the pores of the substrates. Examples of cellulosic non-wovens are described, for example, in U.S. Pat. No. 4,191,609, which is incorporated herein by reference in its entirety. Packages suitable for use herein are any commonly known in the art and include resealable packages and those suitable for one time use. Techniques for combining the wipe substrates with the composition of the present invention are well known in the art. Examples of common techniques include coating, immersing, dipping, sprinkling, or spraying, the wipe substrate with the compositions herein. The composition of the present invention is added to the wipe substrate at a level sufficient to provide the desired malodor neutralization and/or other desired skin benefits.

Uses of the Composition:

As described herein, the composition presented herein can be used to neutralize malodors originating from mucus membranes and occluded skis areas on a human or animal body, and as such it can be used in the treatment of medical or aesthetic conditions in which malodor is a symptom thereof. The composition can also be used in the manufacturing of a product intended for reducing bodily malodors.

According to some embodiments of the present invention, the compositions or products comprising the same, including a bioactive agent or not, are identified for use in neutralizing malodors. In some embodiments, the composition or product is identified for use in neutralizing malodors in a mucus membrane or an occluded skin area in a human.

According to some embodiments of the present invention, the composition is used as a topical formulation that is applied to a particular place on or in the body, as opposed to systemically. Typically, a topical formulation is for application to body surfaces such as the skin or mucous membranes to treat ailments via a large range of classes including but not limited to creams, foams, gels, lotions, and ointments. According to some embodiments of the present invention, the composition is used topically, namely the composition is used on an external mucus membrane or the skin. Regardless of its mode of application, a drug-delivery composition, according to some embodiments of the present invention, may be used as an administration of the drug for an effective systemic effect via the mucus membrane.

For vaginal applications, the composition, according to some embodiments of the present invention, is formulated to adhere to the vaginal mucosa within seconds and remain adhered for several hours or days.

According to an aspect of some embodiments of the resent invention, there is provided a use of the malodor neutralizing composition presented herein for neutralizing malodor in mucous membranes and occluded skin areas.

According to another aspect of embodiments of the present invention, there is provided a method of neutralizing malodor in a subject, which includes contacting mucous membranes and occluded skin areas in the subject with the malodor neutralizing composition presented herein.

HA/NAC Carrier Composition:

The combination of HA and NAC, as these are defined hereinabove, affords a carrier composition that is useful in a variety of applications wherein HA is required as a gel that can stay chemically and mechanically stable under physiological conditions, acidic conditions, and/or under acidic physiological conditions, including conditions where the composition is exposed to HA-degrading enzymes. As discussed hereinabove, NAC inhibits HA-degrading enzymes, as well as lowers the pH, thereby also keeps the HA gel viscous.

Thus, according to an aspect of some embodiments of the present invention, there is provided a carrier composition that includes HA and NAC, and having a pH lower than 6. In some embodiments the pH of the carrier composition is 1, 2, 3, 4, 5 or 6, and any value therebetween.

In some embodiments, the concentration of HA and NAC is set to maintain a viscosity of the carrier composition that ranges from 5 to 30 Pa·s (measured at 1 Hz and 23° C.; see, e.g., Table 9 in Example 1 hereinbelow). In some embodiments the viscosity of the carrier composition is 5, 6, 8, 10, 12, 14, 16, 18, 20, 22, 24, 26, 28 or 30 Pa·s, and any value therebetween.

In some embodiments, the concentration of HA in the carrier composition ranges from 0.1% to 5% by weight of the composition. Optionally, the concentration of HA is about 0.1%, 0.3%, 0.5%, 0.8%, 1%, 1.1%, 1.2%, 1.3%, 1.4%, 1.5%, 1.6%, 1.7%, 1.8%, 1.9%, 2.0%, 2.1%, 2.2%, 2.3%, 2.4%, 2.5%, 2.6%, 2.7%, 2.8%, 2.9%, 3.0%, 3.1%, 3.2%, 3.3%, 3.4%, 3.5%, 3.6%, 3.7%, 3.8%, 3.9%, 4.0%, 4.1%, 4.2%, 4.3%, 4.4%, 4.5%, 4.6%, 4.7%, 4.8%, 4.9% or 5.0%.

In some embodiments, the concentration of NAC in the carrier composition ranges from 0.1% to 10% or from 0.1% to 5% by weight of the composition.

Optionally, the concentration of NAC is about 0.1%, 0.3%, 0.5%, 0.8%, 1%, 1.1%, 1.2%, 1.3%, 1.4%, 1.5%, 1.6%, 1.7%, 1.8%, 1.9%, 2.0%, 2.1%, 2.2%, 2.3%, 2.4%, 2.5%, 2.6%, 2.7%, 2.8%, 2.9%, 3.0%, 3.1%, 3.2%, 3.3%, 3.4%, 3.5%, 3.6%, 3.7%, 3.8%, 3.9%, 4.0%, 4.1%, 4.2%, 4.3%, 4.4%, 4.5%, 4.6%, 4.7%, 4.8%, 4.9%, 5.0%, 6.0%, 7.0%, 8.0%, 9.0% or 10%.

According to some embodiments, the carrier composition presented herein may further include an additional ingredient or agent, such as, without limitation, an aldehyde, a drug or bioactive agent, a fragrance, an antimicrobial agent, a preservative, a pH adjusting agent, a lubricant, a skin aid, an anti-pruritic agent, a colorant, a diluent, a surfactant and a wetting agent, as these are known in the art and/or defined herein.

As used herein, the phrase "bioactive agent" describes a molecule, compound, complex, adduct and/or composite that exerts one or more biological and/or pharmaceutical activities. The bioactive agent can thus be used, for example, to promote wound healing, tissue regeneration, tumor eradication, and/or to prevent, ameliorate or treat various medical conditions.

"Bioactive agent", "pharmaceutically active agent", "pharmaceutically active material", "therapeutic active agent", "biologically active agent", "therapeutic agents", "drug" and other related terms are used interchangeably herein and include, for example, genetic therapeutic agents, non-genetic therapeutic agents, small and large molecules and cells. Bioactive agents useful in accordance with the present invention may be used singly or in any combination. The term "bioactive agent" in the context of the present invention also includes radioactive materials which can serve for radiotherapy, imaging and diagnostics. Exemplary bioactive agents that can be incorporated into the carrier composition provided herein include, without limitation, agonists, amino acids, angiogenesis-promoters, antagonists, antibiotics, antibodies, anti-coagulants, antidepressants, antigens, anti-histamines, anti-hypertensive agents, anti-inflammatory agents, antioxidants, anti-proliferative agents, antisense agents, anti-viral agents, anti-parasite agent, antimicrobial agent, bile acids, cells, chemo-attractants, chemo-repellants, chemokines, chemotherapeutic agents, cholesterol, co-factors, cytokines, DNA, drugs, enzymes, fatty acids, glycolipids, growth factors, haptens, hormones, inhibitors, labeled oligonucleotides, ligands, lipids, nucleic acid constructs, nucleotide-based agents, oligonucleotides, peptides, phospholipids, polysaccharides, proteins, radioisotopes, radiopharmaceuticals, RNA, saccharides, saponins, statins, steroids, toxins, viruses and vitamins.

The composition can be formulated as an ingestible pill or encapsulated substance, or a patch, or an enema, or a suppository, any one of which may incorporate one or more bioactive agents. Exemplary applications include, without limitation, an ingestible bolus for appetite management, or a gastric retention ingestible bolus for drug delivery in cases of local or distant cancer, or delivery of antibiotics for local bacterial infection, intra-uterine or intravaginal treatment, treatment of the urinary bladder for the release of drugs to treat infection, cancer, inflammation or parasites, and the likes. All of the exemplary applications benefit from the low pH, as some are characterized by local acidic environment.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non-limiting fashion.

Example 1

Inhibition of Hyaluronic Acid Degradation

Materials:

Hyaluronic acid (HA) was obtained from Ferring, Israel, as sodium salt, MW $3 \times 10^6$ kDa, 2 ml of 1% HA in PBS as a hydrated gel already in a syringe; or as lyophilized powder (HA 50%) containing the PBS salt.

Hyaluronic acid degrading enzymes included hyaluronidase Type IV-S, from bovine testes (Hyase), obtained from Sigma-Aldrich Israel (Cat. No. H-3884); and chondroitinase ABC (bacterial from *Proteus vulgaris*), obtained from Sigma-Aldrich Israel (Cat. No. C2905).

Hyaluronidase inhibitors included sodium Cromoglycate (SCG) (Cromolyn sodium salt; MW 512), obtained from Sigma-Aldrich Israel (Cat. No. C-0399); tranilast, obtained from Sigma-Aldrich Israel (Cat. No. T-0318; MW 327,33); and N-acetyl L-cysteine (NAC; MW 163.19) was obtained from Sigma-Aldrich Israel (Cat. No. 7250).

Reduced Glutathione (GSH; Glutation reductase; MW 307) was obtained from Sigma-Aldrich Israel (Cat. No. G4251).

Cetylpyridinium chloride (CPC) (Hexadecylpyridinium chloride monohydrate) was obtained from Sigma-Aldrich Israel (Cat. No. C9002); Carbazole (98%) was obtained from BDH (Cat. No. C5132); All other chemicals and solvents were purchased from known vendors, unless otherwise indicated.

The following stock solutions were prepared and used in the following assays, unless otherwise indicated:

HA 1% wt. (10 mg/ml) (HA MW=$3 \times 10^6$ kDa);
Hyase 1 mg/ml;
Chondroitinase ABC (bacterial): 2 U/ml;
Sodium Cromoglycate (SCG) 200 mM;
Tranilast 1 mg/ml;
NAC 400 mM (65.3 mg/ml);
Reduced Glutathione (GSH) 40 mM;
CPC 10% in water;
Carbazole 1% in ethanol.

HA Degradation:

Several methodologies for determining HA degradation, or inhibition thereof, were used, as follows.

Method I (detection of reducing sugars; according to Park and Johnson, 1949, as modified by Halliwell, 1961): Assays were performed following the procedure described in Park and Johnson [J. Biol. Chem., 1949, 181(1), p. 149-51], modified as described in Halliwell [Biochem J., 1961, 79, p. 185-92], in which HA degradation was followed by monitoring the increase in the amount of reducing sugars at the edge of the chains, formed upon HA de-polymerization. The reducing CHO-aldehyde groups exposed at the ends of the HA fragments formed upon HA degradation were reacted with the Park-Johnson/Halliwell reagents.

Method II (Dische's assay; detection of uronic acid residues): Assays were performed by following the procedures described in Dische Z. [J. Biol. Chem., 1947, 167, p. 189-198] and Dische and Rothschild [Anal Biochem., 1967, 21(1), p. 125-30]. In these assays, molecules containing the uronic acid residues found in the precipitate formed upon CPC additions, are re-solubilized and products formed by -sulfuric acid hydrolysis of these fragments are detected by a spectrophotometric assay employing carbazole chromagen reagent. In addition, small residues degraded off the HA chains that have not precipitated with the addition of CPC, can be detected by the carbazole assay performed on the solution, so as to detect all of the uronic acid content.

Evaluation of HA degradation by this method was generally performed as follows:

20 µL of a NAC stock solution, and 20 µL of the stock solutions of the other inhibitors were used in the assay.

200 µL of the HA stock solution were placed in each tube, for achieving a 1 mg HA per tube.

Twenty (20) µL of hyase and 20 µL of NAC were combined and incubated for 2 hours. Then 200 µL of HA (1 mg) were added to each tube and the mixture was incubated at room temperature for 24 hours. Thereafter, the tubes were heated for 2 minutes in boiling water bath and 8 mL of doubled distilled water were added to the tubes as preparation for the Dische's assay.

As per Dische's Assay, 100 µL of 3N NaCl and 0.5 mL of 10% CPC (cetylpyridinium chloride) were thereafter added to each tube and the mixture was incubated at 37° C. until flocculation-turbidity (resulting from precipitation of HA+CPC) could be observed. The mixture was centrifuged for 10 minutes at 10,000 g at room temperature, and the supernatant was thereafter separated from the obtained pellet.

The pellet was dissolved in 1 ml of $CaCl_2$, and the obtained solution was incubated at 37° C. until complete dissolution of the pellet is obtained. A 2:1 v/v ethanol/ether mixture (8 ml) was thereafter added, and the mixture was intensively stirred (by vortex) and kept at −20° C. overnight. The obtained pellet was collected following a centrifugation for 10 minutes at 10,000 g. Then, distilled water (1 mL) was added to solubilize the pellet, followed by addition of 0.2 ml Carbazole 1%. The mixture was stirred thoroughly, and concentrated sulfuric acid (6 mL) was thereafter added.

The samples were transferred into tight closed tubes, placed for 10 minutes in a boiling water bath, and was thereafter cooled in ice until it reached room temperature.

The pink-violet color developed by the chromogen was measured using a spectrophotometer at 527 nm.

Method III (Viscosity of HA): HA at low concentrations (e.g., 1%) in aqueous solution forms a viscous colloidal hydrogel solution, which yields semi-solid gel particles at room temperature and a solid gel at 4° C. HA degradation is therefore evaluated by the loss of the gel gradually from solid gel, to semi solid, to viscous liquid and finally liquefied fluid.

Rheological Measurements:

Rheological properties were determined in a Carri-Med CSL 50 controlled stress rehometer (TA Instruments, Leatherhead, U.K.) operated in cone-plate mode (cone angles 4°, diameter 40 mm). To evaluate the steady-shear viscosity as a function of shear rate, a given shear stress was initially applied and the steady-state shear rate was then measured. A small amplitude oscillatory shear stress test was performed to measure the storage (elasticity) modulus G' of the fluid. To assess viscoelasticity properties of the fluids under conditions relevant to human knee joint movement, frequencies of 0.5 Hz (shear rate 3.14 $s^{-1}$), associated with walking, and 2.5 Hz (15.7 $s^{-1}$) associated with running, were used.

Viscosity measurements were performed a temperature of 23° C. using Brookfield Viscometer DV-II-Pro, with CP-51 spindle at RPM frequency of 0.05-1 Hz, and are expressed as milipascal (mPa) or as Centipoise (CPS). The absolute dynamic viscosity is expressed as: dynamic×second/cm². The procedure was carried out according to Arad et al. Langmuuir 2006, 22, 7313-7317.

Differences between the viscosity (η) and elasticity (G') properties were tested at different concentrations of hyaluronic acid 1% and NAC at different concentrations at room temperature (23° C.). The results for a fluid liquid were in the range of 1-500 mPa S, for a viscous liquid in the range of 1-10 Pa S, for a semi-solid in the range of 50-70 Pa S, and for a solid the results were in the range of 80-100 Pa S and higher.

Results:

Ditch assay, as described hereinabove (Method II) was performed while using the following Hyase inhibitors:
Inhib1: Cromoclycate
Inhib2: Tranilast
Inhib3: NAC
Inhib4: Reduced Glutathione (GSH).

The experiment was run at room temperature (23° C.). Hyase and Inhibitors were incubated first for 2 hours prior to the addition of HA. The results are presented in Table 1 below. Blank tubes included no substrate (HA) and Control tubes included no enzyme, no inhibitor and HA (200 μL). Tubes 5 and 6 contained HA and Hyase with no inhibitor. Standard Solutions with no enzyme and no inhibitor and HA 50 μL and 10 μL were also tested, for calibration. % HA cleaved denotes the weight percent of HA that was degraded. % HA residue denotes the weight percent of non-degraded HA, and represents the % of Hyase inhibition.

TABLE 1

| Tube # | Hyase 20 μL | Inhib1 20 μL | Inhib2 20 μL | Inhib3 20 μL | Inhib 4 20 μL | HA | Net OD at 527 nm | % HA degraded | % HA intact (precipitated) |
|---|---|---|---|---|---|---|---|---|---|
| 1-2 Blank | √ | √ | √ | √ | √ | — | 0 | 0 | 0 |
| 3-4 Control | — | — | — | — | — | 200 μL | 0.258 | 0 | 100 |
| 5-6 | √ | — | — | — | — | 200 μL | 0.000 | 100 | 0 |
| 7-8 | √ | √ | — | — | — | 200 μL | 0.001 | 96.7 | 3.3 |
| 9-10 | √ | — | √ | — | — | 200 μL | 0.026 | 90.2 | 9.8 |
| 11-12 | √ | — | — | √ | — | 200 μL | 0.321 | 0 | 100 |
| 13-14 | √ | — | — | — | √ | 200 μL | 0.045 | 82 | 18 |
| 15-16 Standard 50 ug HA | — | — | — | — | — | 50 μL | 0.287 | 0 | 100 |
| 17-18 Standard 100 ug HA | — | — | — | — | — | 100 μL | 0.658 | 0 | 100 |

As can be seen in Table 1, while some of the Hyase inhibitors only slightly inhibited HA degradation, NAC, final concentration of the incubate 2%; (see Tubes 11-12) completely inhibited HA degradation.

Table 1A below (derived from Table 1) presents the inhibition effect of the various tested inhibitory compounds.

TABLE 1A

| | Inhibitor | % of inhibition of HA degradation |
|---|---|---|
| 1 | NAC | 100 |
| 2 | Reduced Glutation GSH | 18 |
| 3 | Tranilast | 9.8 |
| 4 | Cromoglycate | 3.3 |

The results clearly show the superior inhibition activity of NAC, compared to other Hyase inhibitors.

HA degradation was evaluated using Method III, as described hereinabove. The following gelation ladder was used for the degree of gelation consistency: Solid (highest), semisolid, viscous liquid, fluid liquid (lowest).

HA Gelation in the presence of Hyase Inhibitors, without Hyase was studied while using the following Stock solutions:
HA1%
Sodium Cromoglycate: SCG (200 mM)
Tranilast (1 mg/mL)
Glutation (40 mM)
NAC (400 mM) 6.5%

To each tube containing 2 mL of 1% HA one of the following inhibitors: SCG, Tranilast, and Glutathione (100 μL of each), and NAC (50 μL) was added. The tubes were incubated at 37° C. for 24 hours. No Hyase was present.

Semi-solid HA gels were obtained upon incubation at 37° C. in the presence of all of the tested inhibitors, except glutathione, indicating that these inhibitors have no effect on HA gelation (in the absence of a Hyase). Glutathione had a slight effect on HA gelation and yielded a viscous liquid.

In following assays, at various combinations of a Hyase inhibitor, an HA-degrading enzyme (Hyase or Chondroitinase), incubation temperature, order of addition of the components participating in the reaction, and concentrations were tested.

HA state of gelation was studied in the presence of NAC and various HA-degrading enzymes, using the following Stock solutions:
HA: 1%
Hyase (bovine testes): 1 mg/mL
Chondroitinase ABC (bacterial): 2 U/mL
NAC: 400 mM 6.5%

The tested enzyme (50 μL) was placed in a tube, NAC (50 μL of the Stock solution, final concentration of about 3.3%) was added and the mixture was incubated for 2 hours at room temperature (23° C.). Then, 2 ml of HA 1% were added to each tube and tubes were further incubated at room temperature for additional 24 hours.

The results are presented in Table 2 below. Note that in tubes 5 and 6, 50 μL of PBS were added for achieving the same volume as in the other tubes.

TABLE 2

| Tube No. | Hyase 50 μL | Chondroitinase ABC 50 μL | HA 1% 2 mL | NAC 50 μL | PBS 50 μL | Consistency |
|---|---|---|---|---|---|---|
| 1-2 | √ | — | √ | √ | — | Solid |
| 3-4 | — | √ | √ | √ | — | Solid |
| 5-6 | — | — | √ | — | √ | Solid |
| 7-8 | √ | — | √ | — | — | Fluid liquid |
| 9-10 | — | √ | √ | — | — | Fluid liquid |

As can be seen in Table 2, in the presence of NAC, no effect on HA gelation was observed, for both enzymes, indicating that HA degradation by both enzymes was inhibited. Without NAC and in the presence of the HA-degrading enzymes, HA was degraded.

In a second set of experiments, NAC (50 μL of the Stock solution) was added to a tube containing 2 ml of HA 1%; and the tubes were incubated for 2 hours at room temperature. Then, the HA-degrading enzyme was added and tubes were incubated at room temperature for additional 24 hours. In control tubes 9 and 10 (containing only HA), 50 μL of water were added to achieve the same volume as the other tested tubes.

The results are presented in Table 3 below.

TABLE 3

| Tube No. | HA 1% 2 mL | NAC 50 μL | Hyase 50 μL | Chondroitinase ABC 50 μL | H₂O 50 μL | Consistency |
|---|---|---|---|---|---|---|
| 1-2 | √ | √ | √ | — | — | Fluid Liquid |
| 3-4 | √ | √ | — | √ | — | Solid |
| 5-6 | √ | — | √ | — | — | Fluid Liquid |
| 7-8 | √ | — | — | √ | — | Fluid Liquid |
| 9-10 | √ | — | — | — | √ | Solid |

As can be seen in Table 3, when 50 μL of NAC was added to the HA prior to the addition of Hyase, no inhibition of HA degradation was observed (tubes 1 and 2), indicating that for this enzyme, the inhibition activity of NAC is not exhibited at the low concentration tested (0.5% NAC final concentration). However NAC added to the HA prior to the addition of Chondroitinase ABC, degradation was inhibited, thus indicating that for Chondroitinase ABC the inhibition activity of NAC is exhibited also at the low concentration tested. The low NAC concentration used is similar to the NAC concentration that exhibits anti-oxidation activity. These data therefore indicate that inhibition of HA-degrading enzyme hyaluronidase requires NAC concentration that is higher than the NAC concentration required for exhibiting anti-oxidation activity. For example, it is demonstrated hereinabove that NAC, at 2% final concentration in the reaction mixture, inhibits HA degradation by any of the tested HA-degrading enzymes, thereby indicating that NAC inhibits HA-degrading enzymes at a concentration that is higher by an order of magnitude than the anti-oxidative concentration. Further experiments were performed with higher NAC concentrations.

In another set of experiments, the effect of NAC powder, (at a final concentration of 20%), on HA gelation in the presence of Hyase or Chondroitinase ABC was tested. HA (2 ml of 1%), and the tested enzyme were incubated with and without 400 mg of NAC powder, at 4° C. and at 37° C. The results are presented in Table 4 below.

TABLE 4

| Tube No. | HA 2 cc of 1% | NAC 400 mg dry powder | Hyase 50 μL | Chondroitinase ABC 50 μL | Temp 4° C. | Temp 37° C. | Consistency |
|---|---|---|---|---|---|---|---|
| 1 | √ | — | √ | — | √ | | Fluid liquid |
| 2 | √ | √ | √ | — | √ | | Semisolid |
| 3 | √ | √ | √ | — | | √ | Viscous liquid |
| 4 | √ | — | — | √ | √ | | Fluid Liquid |
| 5 | √ | √ | — | √ | √ | | Semisolid |
| 6 | √ | √ | — | √ | | √ | Viscous liquid |

As can be seen in Table 4, at 4° C. and 20% NAC final concentration, HA degradation was inhibited in the presence of both enzymes. It appears that 20% of NAC is too concentrated and reverse the gelation status at 37° C. Lower NAC concentrations were further tested.

HA gelation in the presence of various concentrations of NAC and/or various concentrations of Hyase was further studies. Lyophilized HA (20 mg of pure HA) was placed in the tubes at room temperature, and a NAC solution of 20%, 10% or 5% (by weight) was added. The solutions were maintained for 24 hours at room temperature, and thereafter Hyase, at various concentrations, was added. Then the mixtures were incubated at room temperature. The enzyme was absent in the control tubes. The results are presented in Table 5 below.

TABLE 5

| Tube No. | HA 40 mg dry powder | NAC (2 mL) | Hyase 50 μL | Hyase 100 μL | Hyase 200 μL | Consistency |
|---|---|---|---|---|---|---|
| 1-2 | √ | 20% √ | √ | — | — | Solid with crystals at the bottom |
| 3-4 | √ | 20% √ | — | √ | — | Solid with crystals at the bottom |
| 5-6 | √ | 20% √ | — | — | √ | Solid with crystals at the bottom |
| 7-8 | √ | 20% √ | — | — | — | Solid with crystals at the bottom |
| 9-10 | √ | 10% √ | √ | — | — | Solid, no crystals |
| 11-12 | √ | 5% √ | √ | — | — | Solid, no crystals |

As can be seen in Table 5, at high concentration of NAC (20%), a complete inhibition of Hyase was observed, even at the highest (200 μL) concentration of the enzyme. Note that the final concentration of HA in all tested samples was 1% as in previous experiments. At such high NAC concentration, appearance of small amount of NAC crystals was observed at the bottom of each tube, along with the solid gel, presumably indicating that NAC solubilization reaches saturation at a concentration of 20% at room temperature. Reducing NAC concentration to 10% or 5% also resulted in inhibition of HA degradation, with no appearance of NAC crystals.

In another set of experiments, the effect of various NAC concentrations on gelation of HA 1% (2 mL in each tube) in the presence of Hyase (50 μL of Stock solution) following incubation at 37° C., was tested, using the same procedure as described hereinabove. The results are presented in Table 6 below.

TABLE 6

| Tube No. | HA 1% 2 mL | NAC concentration | Hyase 50 μL | After 24 h incubation at 37° C. |
|---|---|---|---|---|
| 1-2 | √ | — | √ | Fluid liquid |
| 3-4 | √ | 0.25% (5 mg) | √ | Fluid liquid |
| 5-6 | √ | 0.5% (10 mg) | √ | Fluid liquid |
| 7-8 | √ | 1.0% (20 mg) | √ | Viscous liquid |
| 9-10 | √ | 2.0% (40 mg) | √ | Viscous liquid |
| 11-12 | √ | 4.0% (80 mg) | √ | Semisolid |
| 13-14 | √ | 8% (160 mg) | √ | Semisolid |
| 15-16 | √ | 10% (200 mg) | √ | Semisolid |
| 17-18 | √ | 20% (400 mg) | √ | Fluid liquid |

As can be seen in Table 6, NAC at a concentration lower than 1% fails to inhibit HA degradation, as reflected by the gelation liquefaction status observed in the corresponding tubes. The best effect of NAC was observed at NAC concentration ranging 4-16%, at 37° C. At higher NAC concentration (20%, tubes 17-18), close to saturation, HA was liquefied presumably due to the high NAC concentration which interferes with the gelation status (colloidal instability).

The solubility of NAC crystals in water was measured for different NAC concentrations, at different temperatures. The results are presented in Table 7 below.

TABLE 7

| | Clearance | | |
|---|---|---|---|
| NAC concentration | At 4° C. (storage) | At 23° C., room temperature | At 34-37° C., skin and body temperature |
| 10% | Clear | Clear | Clear |
| 12% | Clear | Clear | Clear |
| 14% | Clear | Clear | Clear |
| 16% | Minimal crystals appearance | Clear | Clear |
| 18% | More crystals | Minimal crystals appearance | Clear |
| 20% | More crystals | More crystals | Clear |

As can be seen in Table 7, NAC at 15% and lower concentration is completely soluble at 23° C. and at lower temperatures, and from 34° C. and up even 20% NAC concentration is completely soluble.

Using the same protocols as above, HA degradation was tested following incubation of HA (2 ml of a 1% Stock solution) and a Hyase inhibitor (20 μL of a stock solution as described hereinabove), at 37° C., in the presence and absence of Hyase. The results are presented in Table 8 below.

TABLE 8

| Tube No. | HA 1% 2cc | Inhibitor 1 SCG | Inhibitor 2 Tranilast | Inhibitor 3 Glutathione | Consistency |
|---|---|---|---|---|---|
| 1-2 at 37° C. | √ | √ | — | — | Semisolid |
| 3-4 at 37° C. | √ | — | √ | — | Semisolid |
| 5-6 at 37° C. | √ | — | — | √ | Viscous liquid |
| 7-8 at 4° C. | √ | √ | — | — | Solid |
| 9-10 at 4° C. | √ | — | √ | — | Solid |
| 11-12 at 4° C. | √ | — | — | √ | Solid |

TABLE 8-continued

| Tube No. | HA 1% 2cc | Inhibitor 1 SCG | Inhibitor 2 Tranilast | Inhibitor 3 Glutathione | Consistency |
|---|---|---|---|---|---|
| 13-14 at 37° C. | √ | — | — | — | Semisolid |
| 15-16 at 4° C. | √ | — | — | — | Solid |

As can be seen in Table 8, at 37° C., HA gelation was independent of the presence of SCG and Tranilast, but Glutathione showed a slight effect of lowering the HA consistency. At 4° C., no differences were noticed on HA gelation properties in the presence of any of the three inhibitors.

Rheological Measurements:

Incubation of HA 1% with different concentrations of NAC was performed as described hereinabove, and the viscosity and elasticity of the obtained compositions were measured as described in the method section hereinabove. The results are presented in Table 9 below.

TABLE 9

| | % HA | % NAC | Viscosity at 1 Hz, 23° C., in Pa · s | Elasticity G' at 1 Hz, 23° C., in Pa · s | Loss Modulus G" at 1 Hz, 23° C., in Pa · s |
|---|---|---|---|---|---|
| N-1 | 1 | 0 | 5 | 118 | 37 |
| N-2 | 1 | 1 | 5 | 110 | 34 |
| N-3 | 1 | 2 | 30 | 178 | 178 |
| N-4 | 1 | 4 | 30 | 167 | 45 |
| N-5 | 1 | 10 | 10 | 170 | 55 |
| N-6 | 1 | 20 | 2 | 22 | 26 |

The change in the rheology properties of the HA/NAC compositions was preserved in the time course of weeks at room temperature and at 4° C. As can be seen in Table 9, the highest viscosity (η) was observed for N-3: 2% NAC, N-4: 4% NAC and then N-5: 10% NAC. The highest elasticity (G') was observed for N-3: 2% NAC and then N-5: 10% NAC and N-4: 4% NAC. The highest loss of Modulus (G") was observed for N-5: 10% NAC and then for N-4: 4% NAC and N-3: 2% NAC.

It is noted that for all of the tested parameters, values increase as the concentration increase up to 10% NAC (from N-1 to N-5), yet, at 20% NAC (N-6) all values are lower than N-1 (0% NAC).

NAC derivatives, such as L-cysteine, D-cysteine, N-acetyl-L cysteine, N-acetyl-D-cysteine, NAC-amide, reduced glutathione, Nacystelyn (NAL; a lysine salt of NAC), S-Methyl-L-cysteine, γ-L-Glutamyl-L-cysteine, S-Allyl-d5-L-cysteine, S-Carboxymethyl-L-Cysteine/Carbocistein, are tested for their effect on HA degradation. Following the same procedures as described, the tested NAC derivative (at a concentration within a range of e.g., 1-20% wt.) and the tested HA-degrading enzyme (e.g., Hyase; at a concentration as presented hereinabove) are added to each tube, HA (e.g., 2 ml of 1% stock solution) is thereafter added and the tubes are incubated at room temperature for 24 hours.

In conclusion, the studies show that in order to inhibit HA degradation under physiological conditions and keep the composition acidic, NAC should be present in the composition at a concentration of at least 0.1%, and not higher than 5 or 10%. As stated hereinabove, NAC plays a role in setting the low pH and high viscosity of the composition.

Example 2

Malodor Neutralization by Aldehyde

Materials:

Myrac aldehyde (MA), N-acetylcysteine (NAC), hyaluronic acid sodium salt (HA) and trimethylamine (TMA) were obtained from Sigma-Aldrich Israel.

Fish samples were obtained at a local fish store.

Methods:

The experimental system for following the neutralization of an exemplary malodorous compound trimethylamine (TMA) by an exemplary malodor neutralizing agent aldehyde myrac aldehyde, was based on assaying the CHO functional group using the Park-Johnson method [Park, J. T. and Johnson, M. J., *J. Biol. Chem.*, 1949, 181, p. 149]. TMA levels were analyzed using Siemens Multistix 10 SG reagent strips.

In order to estimate the concentrations of TMA with which the malodor neutralizing composition, according to embodiments of the present invention, would be contacted, the inventors have studied TMA levels that are generally exhibited in human subjects. For example, TMA levels in the urine of healthy subjects and of trimethylaminuria patients is available from the literature [Yamazaki, H. et al., *Life Sci.*, 2004, 74(22), p. 2739-47; Shimuzu, M. et al., *Drug Metab Pharmacokinet.*, 2009, 24(6), p. 549-52]. Urine samples were analyzed for the quantification of TMA, TMAO and creatinine, and the results were expressed as a ratio of micromole TMA/milimole creatinine and micromol TMA per micromole creatinine, based on H-NMR spectrum [Maschke, S. et al., *Clin Chim Acta.*, 1997, 263(2), p. 139-46].

From these studies it was estimated that the concentration of TMA in the mucus of normal human subjects is about 2 mM. It was further estimated that the molar ratio of aldehyde to amine would be in the range of 80-180 molar excess of aldehyde over amine in order to obtain acceptable neutralization of the amine smell, and thus, in some embodiments, the molar ratio of aldehyde to amine is about 130 to 1.

Determination of the concentration of myrac aldehyde needed to neutralize TMA malodor was evaluated by smelling 2 ml samples of an aqueous solution containing 2 mM TMA (4 micromole of TMA in 2 ml of water). Malodor/odor neutralizing tests were performed using a series of aldehyde concentration of 1, 10, 20, 40 and 80 microliter of pure aldehyde, and the results are presented in Table 10.

TABLE 10

| Sample No. | μl aldehyde in 2 ml TMA 2 mM solution | Percent aldehyde in sample | Perceived scent |
| --- | --- | --- | --- |
| 1 | 2 | 0.1 | Strong fishy |
| 2 | 10 | 0.5 | fishy |
| 3 | 20 | 1 | Faint fishy |
| 4 | 40 | 2 | No scent |
| 5 | 80 | 4 | Faint myrac |
| 6 | 100 | 5 | Myrac |
| 7 | 200 | 10 | Myrac |
| 8 | 300 | 15 | Strong Myrac |
| 9 | 400 | 20 | Strong myrac |

It was determined that about 2% myrac aldehyde can neutralize the smell of TMA, and from 4% and up the scent of myrac aldehyde is perceived and masks the smell of TMA.

Based on the above, exemplary compositions comprising up to 3% HA, up to 2% NAC and at least 1% MA in distilled water, optionally combine with a fragrance, color or other additives, and set to a pH lower than 6, and a consistency ranging from fluid to sticky gel, were prepared. In some embodiments, the compositions are formulated as coated or uncoated vaginal tablets or suppository for introduction into the vaginal virtual cavity. In some embodiments, the compositions are formulated as creams, ointments and gels for spreading on the mucus membrane.

Example 3

In Vitro Tests

In order to test the effectiveness of the compounds presented herein, in vitro tests were performed using amine-derived malodors originating from ammonia (a piece of cloth soaked in ammonia) and from a sample of decomposed raw fish.

An exemplary malodor neutralizing composition comprising 0.2% HA sodium salt in water (at least about 1,000 KD MW), 0.1% of NAC (pure pharmaceutical grade, NUTRABIO Inc.), 1% pure MA, and 0.5% fragrance (rose extract), set to a pH of 6, was used in the form of a sprayable topical fluid embodiment, which was applied over a piece of cloth soaked with ammonia, or over a piece of decomposed fish.

In both cases, two strokes of the spray over the decomposing fish sample were sufficient to neutralize the malodor.

Example 4

In Vivo Tests and Experience

An exemplary malodor neutralizing composition comprising 0.2% HA sodium salt in water (at least about 1,000 KD MW), 0.1% of NAC (pure pharmaceutical grade, NUTRABIO Inc.), 1% pure MA, and 0.5% fragrance (rose extract), set to a pH of 6, was used in the form of a sprayable topical fluid embodiment.

A group of 20 healthy adult female volunteers, ages 18-40, who complained about unpleasant genital odor, were asked to apply samples of the malodor neutralizing compositions provided herein.

After a shower with local cleaning of the genital area, the volunteers were asked to apply the gel composition by spraying three strokes of the composition onto the vulva and within the major labia to try to reach a large area. The operation was performed in the morning and was only repeated at night after a second shower if the volunteer intended to be active again that day. The procedure was repeated for 4 consecutive days.

The volunteers were asked to rate the experience in terms of adverse effects, such as local discomfort, skin or mucosal reaction, irritation, rash, itchiness or any other adverse response to the composition. All volunteers reported no local reaction to the composition after immediate and extended use of the composition.

The volunteers were asked to rate the experience in terms of efficacy, such as reduction of vaginal malodor in response to the use of the composition. All volunteers reported a notable reduction of vaginal malodor after immediate and extended use of the composition.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A method of neutralizing vaginal malodor in a subject in need thereof, comprising contacting a vaginal mucous membrane with an aqueous malodor neutralizing composition that comprises hyaluronic acid or a salt thereof (HA), N-acetyl cysteine or a pharmaceutically or cosmetically acceptable derivative thereof (NAC), and a pharmaceutically or cosmetically acceptable aldehyde, and has a pH equal or lower than 6.

2. The method of claim 1, wherein
said hyaluronic acid or a salt thereof is hyaluronic acid sodium salt, and said aldehyde is myrac aldehyde.

3. The method of claim 1, wherein a concentration of said HA in said composition ranges from 0.1% to 5% by weight of the total weight of said composition.

4. The method of claim 1, wherein a concentration of said NAC in said composition is an inhibitory effective amount with respect to enzymatic degradation of said HA, and ranges from 0.1% to 10% by weight of the total weight of said composition.

5. The method of claim 1, wherein a concentration of said aldehyde in said composition ranges from 0.1% to 10% by weight of the total weight of said composition.

6. The method of claim 5, wherein said aldehyde is a non-fragrant aldehyde.

7. The method of claim 5, wherein said aldehyde is a fragrant aldehyde.

8. The method of claim 5, wherein said aldehyde is myrac aldehyde.

9. The method of claim 2, wherein said composition further comprises an additional agent selected from the group consisting of a fragrance, an antimicrobial agent, a bioactive agent, a spermicide, a preservative, a pH adjusting agent, a lubricant, a skin aid, an anti-pruritic agent, a colorant, a diluent, a surfactant and a wetting agent.

* * * * *